(12) United States Patent
Yee et al.

(10) Patent No.: US 12,735,470 B2
(45) Date of Patent: Sep. 15, 2026

(54) ENGINEERED T CELL RECEPTORS AND METHODS OF USE

(71) Applicant: BOARD OF REGENTS, THE UNIVERSITY OF TEXAS SYSTEM, Austin, TX (US)

(72) Inventors: Cassian Yee, Houston, TX (US); Ke Pan, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 817 days.

(21) Appl. No.: 18/001,185

(22) PCT Filed: Jun. 8, 2021

(86) PCT No.: PCT/US2021/036443

§ 371 (c)(1),
(2) Date: Dec. 8, 2022

(87) PCT Pub. No.: WO2021/252517

PCT Pub. Date: Dec. 16, 2021

(65) Prior Publication Data

US 2023/0227526 A1 Jul. 20, 2023

Related U.S. Application Data

(60) Provisional application No. 63/036,539, filed on Jun. 9, 2020.

(51) Int. Cl.

| | |
|---|---|
| ***A61K 40/32*** | (2025.01) |
| ***A61K 40/11*** | (2025.01) |
| ***A61K 40/42*** | (2025.01) |
| ***A61P 35/00*** | (2006.01) |
| ***C07K 14/705*** | (2006.01) |
| ***C12N 5/0783*** | (2010.01) |
| *A61K 38/00* | (2006.01) |

(52) U.S. Cl.

CPC .......... *C07K 14/7051* (2013.01); *A61K 40/11* (2025.01); *A61K 40/32* (2025.01);
(Continued)

(58) Field of Classification Search
None
See application file for complete search history.

(56) References Cited

U.S. PATENT DOCUMENTS

| | | | |
|---|---|---|---|
| 10,526,407 | B2 | 1/2020 | Alten et al. |
| 2005/0010030 | A1 | 1/2005 | Zang et al. |

(Continued)

FOREIGN PATENT DOCUMENTS

| | | |
|---|---|---|
| CN | 105001339 | 10/2015 |
| CN | 112566698 | 3/2021 |

(Continued)

OTHER PUBLICATIONS

Rudikoff et al., "Single amino acid substitution altering antigen-binding specificity," Proc Natl Acad Sci USA 79:1979-1983 (Year: 1982).*

(Continued)

*Primary Examiner* — M Franco G Salvoza
(74) *Attorney, Agent, or Firm* — NORTON ROSE FULBRIGHT US LLP

(57) ABSTRACT

This disclosure provides for engineered T cell Receptors (TCRs), cells comprising the TCRs, and methods of making and using the TCRs. The current disclosure relates to TCRs that specifically recognize epitope(s) from tumor antigen COL6A3. Accordingly, aspects of the disclosure relate to an engineered T-cell Receptors (TCRs), nucleic acids encoding the TCRs, and cells comprising the nucleic acids and TCRs. Also provided are compositions comprising the cells, nucleic acids, or engineered TCRs of the disclosure, methods of making the cells and methods of using the embodiments of the disclosure for therapeutic treatments.

16 Claims, 8 Drawing Sheets

Specification includes a Sequence Listing.

(52) U.S. Cl.
CPC .......... *A61K 40/4202* (2025.01); *A61P 35/00* (2018.01); *C12N 5/0636* (2013.01); *A61K 38/00* (2013.01); *C07K 2319/00* (2013.01)

(56) References Cited

U.S. PATENT DOCUMENTS

| | | | |
|---|---|---|---|
| 2017/0145070 | A1 | 5/2017 | Hinrichs et al. |
| 2019/0062398 | A1 | 2/2019 | Blanketnstein et al. |
| 2019/0321401 | A1 | 10/2019 | Goldfless et al. |
| 2020/0010804 | A1 | 1/2020 | Nakatsura et al. |

FOREIGN PATENT DOCUMENTS

| | | |
|---|---|---|
| WO | WO 2017/193104 | 11/2017 |
| WO | WO 2019/036688 | 2/2019 |
| WO | WO 2019/086665 | 5/2019 |

OTHER PUBLICATIONS

Wong et al., “Comparative Analysis of the CDR Loops of Antigen Receptors,” Front. Immunol. 10:2454 (Year: 2019).*

Manning et al., “Alanine Scanning Mutagenesis of an αβ T Cell Receptor: Mapping the Energy of Antigen Recognition,” Immunity vol. 8: 413-425 (Year: 1998).*

International Search Report and Written Opinion issued in corresponding International application PCT/US2021/036443 mailed Oct. 28, 2021.

Extended European Search Report issued in corresponding European U.S. Appl. No. 21/822,596, dated May 21, 2024.

Mccormack et al. “Bi-specific TRC-anti CD3 redirected T-cell targeting of NY-ESO-1- and LAGE-1-positive tumors”, Cancer Immunology, Immunotherapy, vol. 62, No. 4, pp. 773-785, 2012.

Hutt et al. “Affinity Maturation and Validation of a COL6A3-002-Specific T Cell Receptor for Improving Performance in Adoptive Cell Therapy”. Protein Engineering Summit, 10th Annual PEGS Europe 2018, p. 118, Jun. 2023.

* cited by examiner

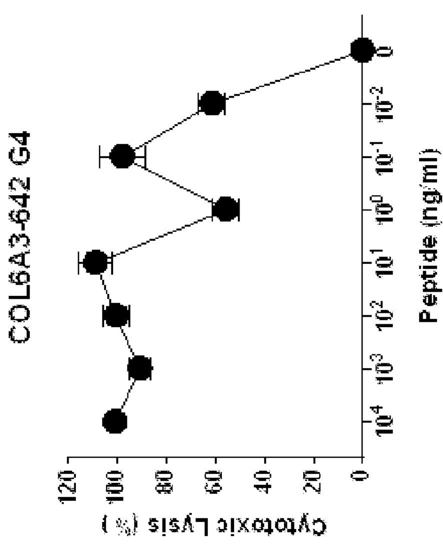
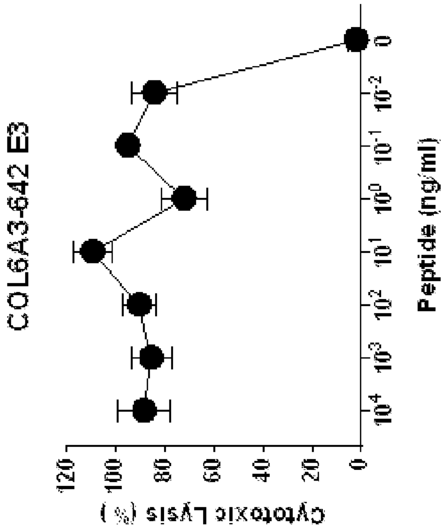
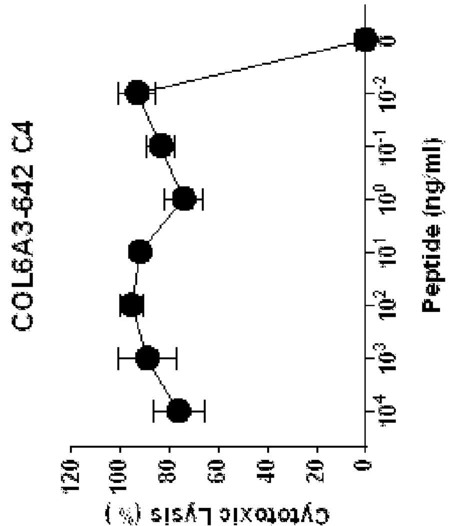
FIG. 2

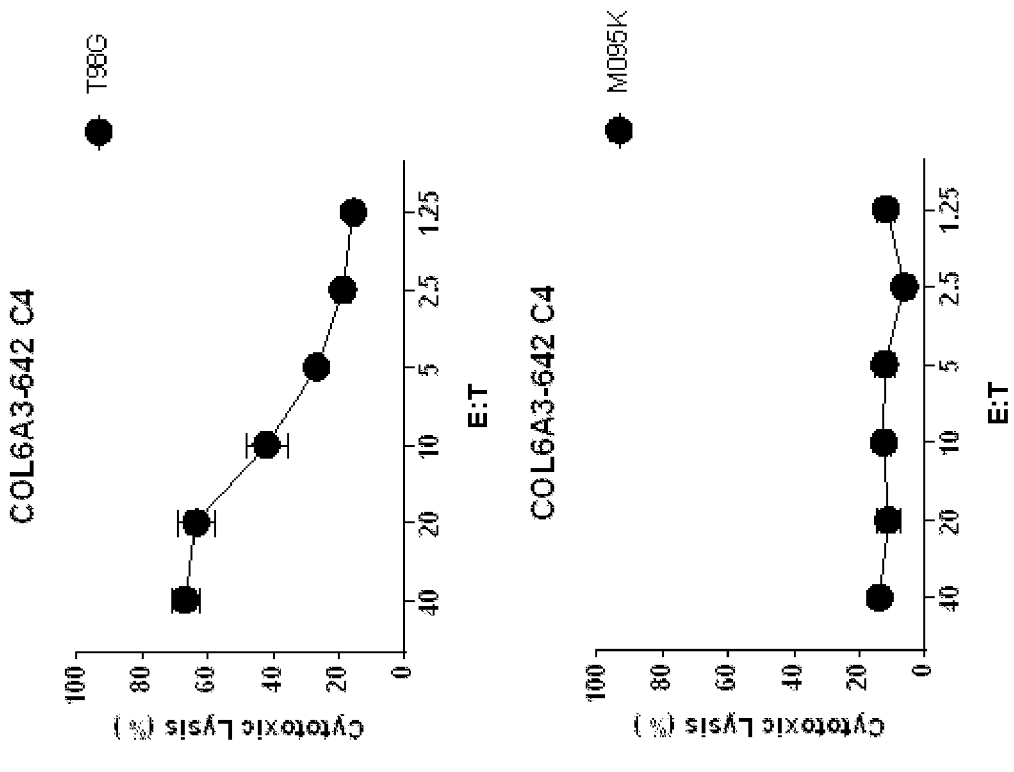
FIG. 3A
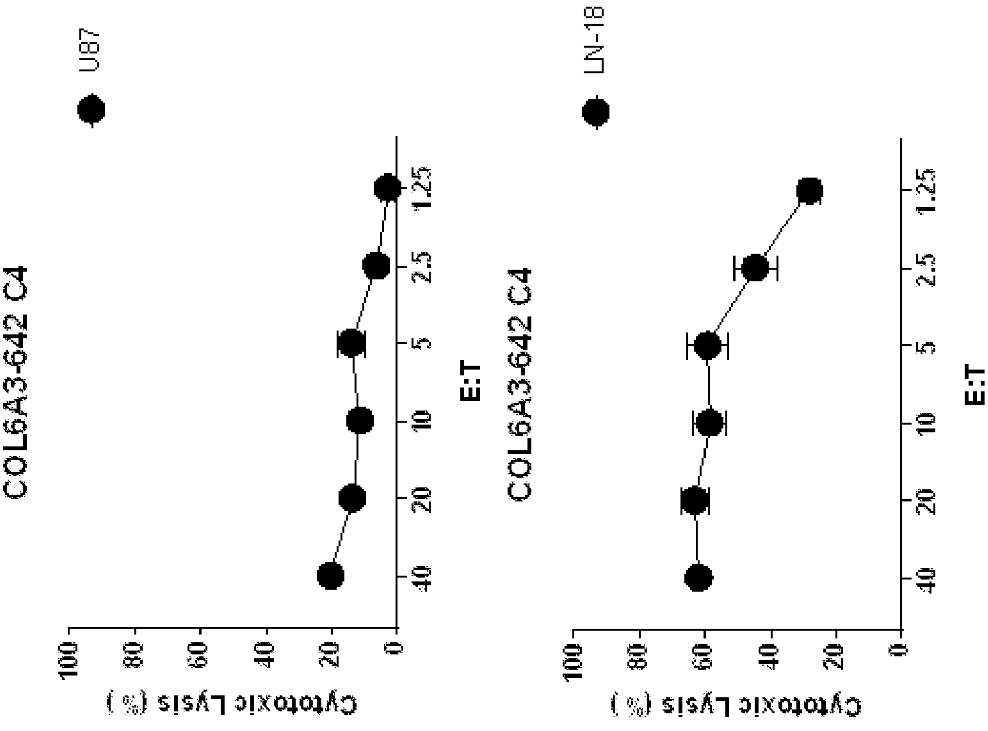

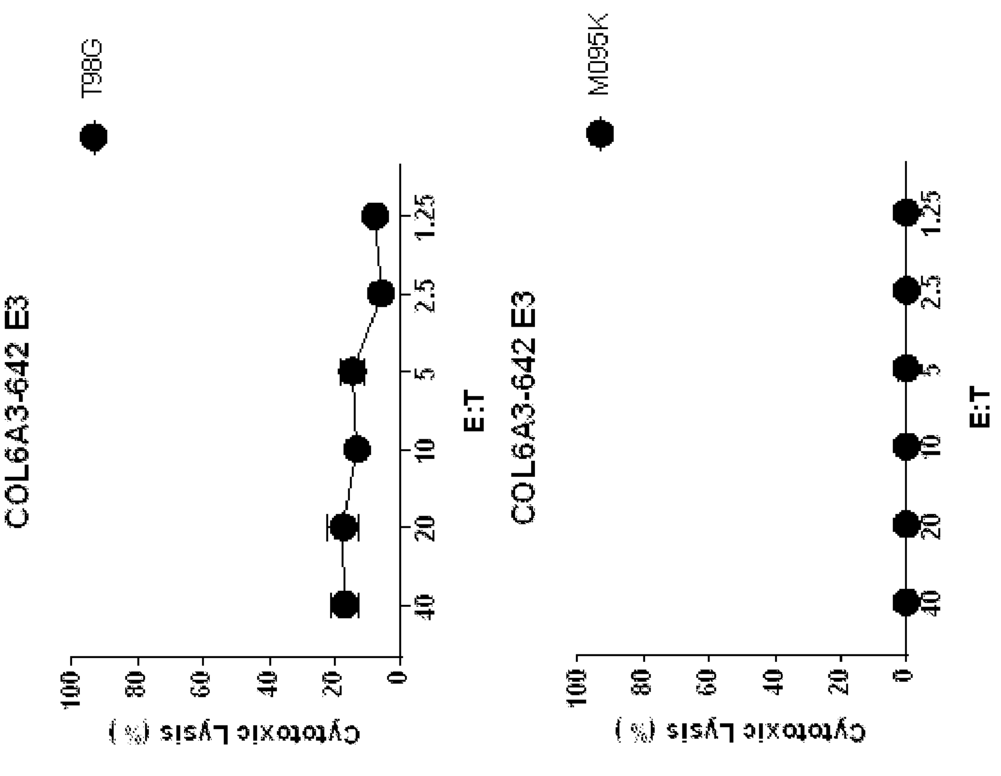
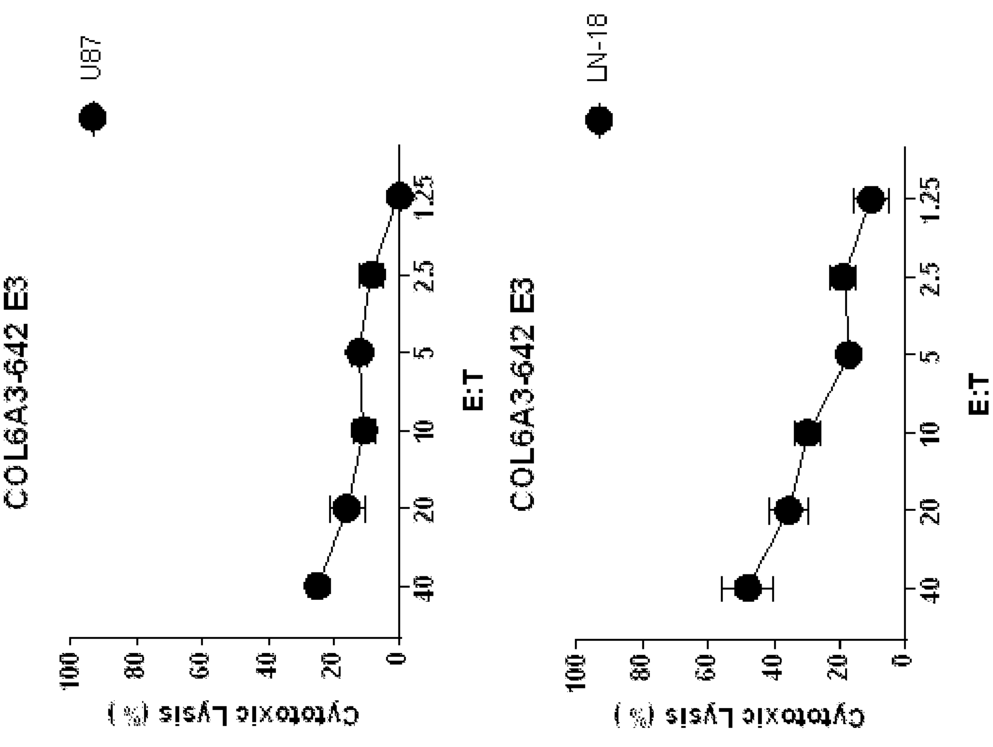
FIG. 3B

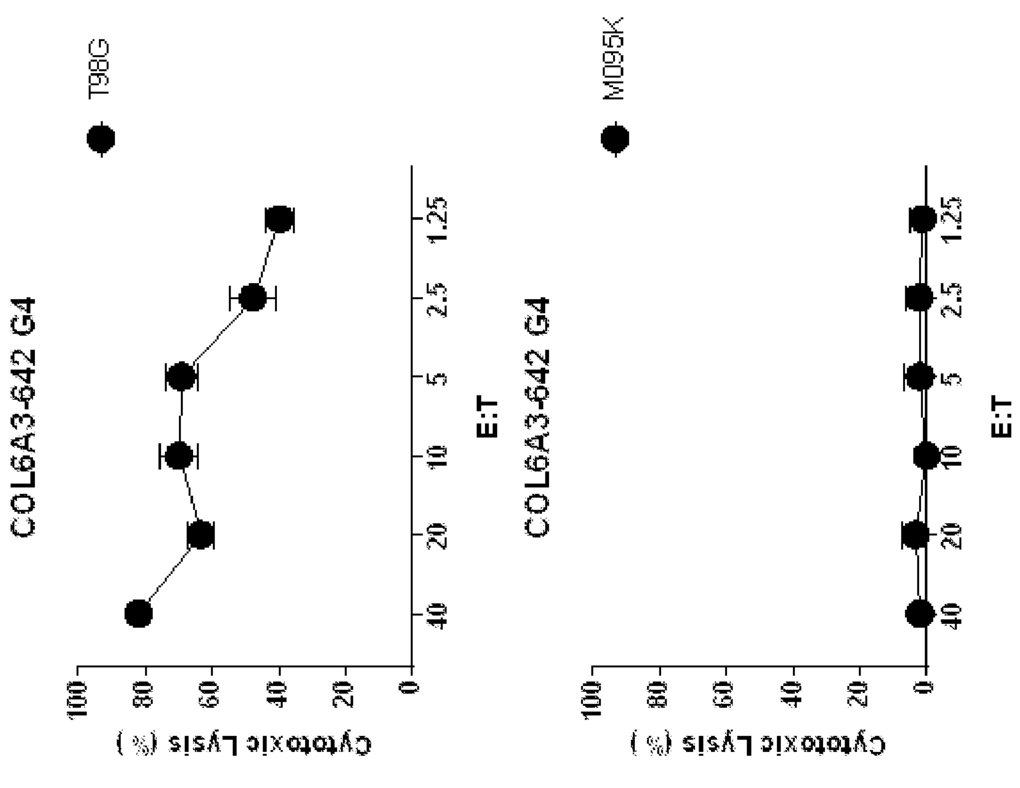
FIG. 3C
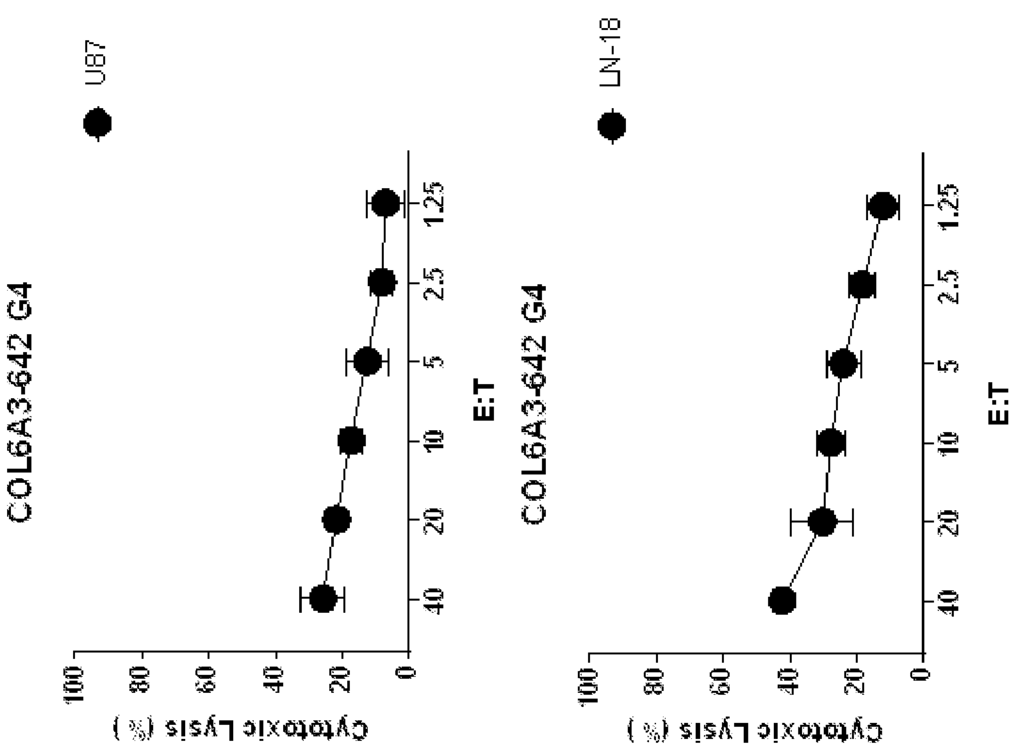

FIG. 5A-E

SEQUENCE LISTING

```
<160> NUMBER OF SEQ ID NOS: 17

<210> SEQ ID NO 1
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgtggggag ttttccttct ttatgtttcc atgaagatgg gaggcactac aggacaaaac      60

attgaccagc ccactgagat gacagctacg gaaggtgcca ttgtccagat caactgcacg     120

taccagacat ctgggttcaa cgggctgttc tggtaccagc aacatgctgg cgaagcaccc     180

acatttctgt cttacaatgt tctggatggt ttggaggaga aaggtcgttt ttcttcattc     240
```

```
cttagtcggt ctaaagggta cagttacctc cttttgaagg agctccagat gaaagactct    300

gcctcttacc tctgtgctgt gagggccgac agaggctcaa ccctggggag gctatacttt    360

ggaagaggaa ctcagttgac tgtctggcct gatatccaga accctgaccc tgccgtgtac    420

cagctgagag actctaaatc cagtgacaag tctgtctgcc tattcaccga ttttgattct    480

caaacaaatg tgtcacaaag taaggattct gatgtgtata tcacagacaa aactgtgcta    540

gacatgaggt ctatggactt caagagcaac agtgctgtgg cctggagcaa caaatctgac    600

tttgcatgtg caaacgcctt caacaacagc attattccag aagacacctt cttccccagc    660

ccagaaagtt cctgtgatgt caagctggtc gagaaaagct ttgaaacaga tacgaaccta    720

aactttcaaa acctgtcagt gattgggttc cgaatcctcc tcctgaaagt ggccgggttt    780

aatctgctca tgacgctgcg gctgtggtcc agctaa                              816
```

<210> SEQ ID NO 2
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atgggcttca ggctcctctg ctgtgtggcc ttttgtctcc tgggagcagg cccagtggat     60

tctggagtca cacaaacccc aaagcacctg atcacagcaa ctggacagcg agtgacgctg    120

agatgctccc ctaggtctgg agacctctct gtgtactggt accaacagag cctggaccag    180

ggcctccagt tcctcattca gtattataat ggagaagaga gagcaaaagg aaacattctt    240

gaacgattct ccgcacaaca gttccctgac ttgcactctg aactaaacct gagctctctg    300

gagctggggg actcagcttt gtatttctgt gccagcagcg tagacggggg ggcctcgggg    360

gagcagttct tcgggccagg gacacggctc accgtgctag aggacctgaa aaacgtgttc    420

ccacccgagg tcgctgtgtt tgagccatca gaagcagaga tctcccacac ccaaaaggcc    480

acactggtgt gcctggccac aggcttcttc cctgaccacg tggagctgag ctggtgggtg    540

aatgggaagg aggtgcacag tggggtcagc acggacccgc agcccctcaa ggagcagccc    600

gccctcaatg actccagata ctgcctgagc agccgcctga gggtctcggc caccttctgg    660

cagaaccccc gcaaccactt ccgctgtcaa gtccagttct acgggctctc ggagaatgac    720

gagtggaccc aggatagggc caaacccgtc acccagatcg tcagcgccga ggcctggggt    780

agagcagact gtggctttac ctcggtgtcc taccagcaag ggtcctgtc tgccaccatc     840

ctctatgaga tcctgctagg gaaggccacc ctgtatgctg tgctggtcag cgcccttgtg    900

ttgatggcca tggtcaagag aaaggatttc taa                                 933
```

<210> SEQ ID NO 3
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
```

```
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Arg Ala Asp Arg Gly
            100                 105                 110

Ser Thr Leu Gly Arg Leu Tyr Phe Gly Arg Gly Thr Gln Leu Thr Val
        115                 120                 125

Trp Pro Asp Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270


<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
            20                  25                  30

Phe Trp Tyr Gln Gln His Ala Gly Glu Ala Pro Thr Phe Leu Ser Tyr
        35                  40                  45

Asn Val Leu Asp Gly Leu Glu Glu Lys Gly Arg Phe Ser Ser Phe Leu
    50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Arg Ala Asp Arg Gly Ser
                85                  90                  95

Thr Leu Gly Arg Leu Tyr Phe Gly Arg Gly Thr Gln Leu Thr Val Trp
            100                 105                 110
```

Pro Asp

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Met Trp Gly Val Phe Leu Leu Tyr Val Ser Met Lys Met Gly Gly Thr
1 5 10 15

Thr

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Thr Ser Gly Phe Asn Gly
1 5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Asn Val Leu Asp Gly Leu
1 5

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Ala Val Arg Ala Asp Arg Gly Ser Thr Leu Gly Arg Leu Tyr
1 5 10

<210> SEQ ID NO 9
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Gly Phe Arg Leu Leu Cys Cys Val Ala Phe Cys Leu Leu Gly Ala
1 5 10 15

Gly Pro Val Asp Ser Gly Val Thr Gln Thr Pro Lys His Leu Ile Thr
20 25 30

Ala Thr Gly Gln Arg Val Thr Leu Arg Cys Ser Pro Arg Ser Gly Asp
35 40 45

```
Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Asp Gly Gly Ala Ser Gly Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310


<210> SEQ ID NO 10
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Val Asp
```

```
                85                  90                  95

Gly Gly Ala Ser Gly Glu Gln Phe Phe Gly Pro Gly Thr Arg Leu Thr
            100                 105                 110

Val Leu


<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gly Phe Arg Leu Leu Cys Cys Val Ala Phe Cys Leu Leu Gly Ala
1               5                   10                  15

Gly Pro Val


<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Asp Leu Ser
1               5


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Tyr Asn Gly Glu Glu
1               5


<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ser Ser Val Asp Gly Gly Ala Ser Gly Glu Gln Phe
1               5                   10


<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Leu Leu Asp Gly Ser Ala Asn Val
1               5
```

```
<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ala Val Arg Ala Asp Arg Gly Ser Thr Leu Gly Arg Leu Tyr Phe
1               5                   10                  15


<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ala Ser Ser Val Asp Gly Gly Ala Ser Gly Glu Gln Phe Phe
1               5                   10                  15
```

ENGINEERED T CELL RECEPTORS AND METHODS OF USE

This application is a national phase application under 35 U.S.C. § 371 of International Application No. PCT/US2021/036443, filed Jun. 8, 2021, which claims benefit of priority of U.S. Provisional Application No. 63/036,539, filed Jun. 9, 2020, both of which are hereby incorporated by reference in their entirety.

SEQUENCE LISTING

The application contains a Sequence Listing which has been filed electronically in compliance with ST.25 format and is hereby incorporated by reference in its entirety. Said Sequence Listing, created on Dec. 7, 2022 is named MDACP1236US_SL and is 13,220 bytes in size.

BACKGROUND OF THE INVENTION

I. Field of the Invention

This invention relates to the field of cancer therapy.

II. Background

Adoptive T-cell therapy is one potentially powerful treatment for cancer that genetically modifies natural T cells to make them tumor-specific and to improve their ability to destroy tumor cells. The genetically modified T cells are able to express chimeric antigen receptors (CARs) or T-cell receptors (TCRs), showing impressive results in multiple clinical trials. TCR-engineered T (TCR-T) cells have shown great promise against tumors. The potency of TCRs relies on their interaction with peptide-major histocompatibility complex (pMHC), complexes formed by peptide bound to MHC. Intracellular antigens are cut up into peptide chains and displayed by MHC molecules to form pMHCs. Cytoplasmic proteins to be expressed by class I MHC proteins, most of which are defective ribosomal translation products, are cleaved into peptide chains by proteolysis. These peptides are then bound to class I MHC proteins, which are expressed on all nucleated cells' cell surface. Some cells, called antigen-presenting cells (APCs), express class II MHC proteins. They internalize foreign material proteins by endocytosis and cleave them into peptide chains to bind with class II MHC proteins T-cell receptors from T cells, which must be matched to human leukocyte antigen (HLA) alleles of patients, recognize these pMHCs and cause the killing of cancer cells. (Human class I MHC protein is expressed from 3 gene regions: HLA-A, HLA-B, and HLA-C, and human class II MHC protein is also expressed from 3 gene regions: HLA-DR, HLA-DP, and HLA-DQ.) There is a need for the engineering of TCRs that are directed to cancer-specific antigens and useful for the treatment of cancer.

SUMMARY OF THE INVENTION

This disclosure provides for engineered T cell Receptors (TCRs), cells comprising the TCRs, and methods of making and using the TCRs. The current disclosure relates to TCRs that specifically recognize the epitope: FLLDGSANV (SEQ ID NO:15) from tumor antigen COL6A3. Accordingly, aspects of the disclosure relate to a polypeptide comprising an antigen binding variable region comprising a CDR3 comprising an amino acid sequence with at least 80% sequence identity to AVRADRGSTLGRLY (SEQ ID NO:8).

Other aspects relate to a polypeptide comprising an antigen binding variable region comprising a CDR3 comprising an amino acid sequence with at least 80% sequence identity to ASSVDGGASGEQF (SEQ ID NO:14).

The disclosure also provides for T-cell receptors (TCR) and engineered TCRs, such as a TCR comprising a TCR-a polypeptide and a TCR-b polypeptide, wherein the TCR-a polypeptide comprises a CDR3 comprising an amino acid sequence with at least 80% sequence identity to AVRADRGSTLGRLY (SEQ ID NO:8) and the TCR-b polypeptide comprises a CDR3 comprising an amino acid sequence with at least 80% sequence identity to

```
                                        (SEQ ID NO: 14)
ASSVDGGASGEQF
```

Yet further aspects relate to nucleic acids encoding the polypeptides and engineered TCRs, nucleic acid vectors comprising one or more nucleic acids of the disclosure, and cells comprising the polypeptides, engineered TCRs and/or nucleic acids of the disclosure. Also provided are compositions comprising the polypeptides, cells, nucleic acids, or engineered TCRs of the disclosure. Further aspects relate to a method of making an engineered cell comprising transferring a nucleic acid or vector of the disclosure into a cell. Further aspects relate to a method for treating cancer in a subject comprising administering a polypeptide, composition, cell, nucleic acid, or engineered TCR to a subject in need thereof. Methods also include methods of reducing tumor burden; methods of lysing a cancer cell; methods of killing tumor/cancerous cells; methods of increasing overall survival; methods of reducing the risk of getting cancer or of getting a tumor; methods of increasing recurrent free survival; methods of preventing cancer; and/or methods of reducing, eliminating, or decreasing the spread or metastasis of cancer, the method comprising administering a polypeptide, composition, cell, nucleic acid, or engineered TCR to a subject in need thereof.

Further aspects relate to a fusion protein comprising a TCR of the disclosure and a CD3 binding region. The CD3 binding region may comprise a CD3-specific fragment antigen binding (Fab), single chain variable fragment (scFv), single domain antibody, or single chain antibody. Exemplary CD3-specific fragment antigen binding (Fab) are known in the art. For example, US20180222981, which is herein incorporated by reference, discloses variable regions that bind specifically to CD3, which may be used in aspects s of this disclosure. Anti-CD3 antibodies and variable regions are disclosed in US20180117152, which is also incorporated by reference.

The polypeptide of the disclosure or the TCR-a polypeptide may comprise a CDR 3 comprising an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:8. The polypeptide may comprise a CDR 3 comprising an amino acid sequence of SEQ ID NO:8. The polypeptide of the disclosure or the TCR-b polypeptide may comprise a CDR3 comprising an amino acid sequence with at least or exactly 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to ASSVDGGASGEQF (SEQ ID NO:14). The polypeptide of the disclosure or the TCR-b polypeptide may comprise a CDR3 comprising an amino acid sequence of SEQ ID NO:14. The engineered TCR may comprise a TCR-a polypeptide comprising a CDR 3 having an amino acid of SEQ ID NO:8 and a TCR-b polypeptide comprising a CDR3 comprising an amino acid sequence of SEQ ID NO:14.

The polypeptide may comprise a variable region comprising a CDR1, CDR2, and CDR3 from a TCR-a polypeptide and/or a TCR-b polypeptide. The variable region may comprise a CDR1 with at least 80% sequence identity to TSGFNG (SEQ ID NO:6). In some aspects, the variable region comprises a CDR1 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:6. In some aspects, the variable region comprises a CDR2 with at least 80% sequence identity to NVLDGL (SEQ ID NO:7). The variable region may comprise a CDR2 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:7. The variable region may comprise a CDR1 comprising the amino acid sequence of SEQ ID NO:6 and/or a CDR2 comprising the amino acid sequence of SEQ ID NO:7. The variable region may comprise an amino acid sequence with at least 70% sequence identity to SEQ ID NO:4. In some aspects, the variable region comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:4. In some aspects, the variable region comprises the amino acid sequence of SEQ ID NO:4. In some aspects, the polypeptide comprises a T cell receptor alpha (TCR-a) variable region. In some aspects, the polypeptide comprises a TCR-a variable and constant region. The polypeptide may further comprise a signal peptide. The signal peptide may comprise an amino acid sequence with at least 80% identity to SEQ ID NO:5. In some aspects, the signal peptide comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:5. In some aspects, the signal peptide comprises an amino acid sequence of SEQ ID NO:5. In some aspects, the variable region comprises a CDR1, CDR2, and/or CDR3.

The variable region may comprise a CDR1 with at least 80% sequence identity to SGDLS (SEQ ID NO:12). In some aspects, the variable region comprises a CDR1 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:12. The variable region may comprise a CDR2 with at least 80% sequence identity to YYNGEE (SEQ ID NO:13). In some aspects, the variable region comprises a CDR2 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:13 The variable region may comprise a CDR1 comprising the amino acid sequence of SEQ ID NO:12 and/or a CDR2 comprising the amino acid sequence of SEQ ID NO:13. In some aspects, the variable region comprises an amino acid sequence with at least 70% sequence identity to SEQ ID NO:10. In some aspects, the variable region comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:10. In some aspects, the variable region comprises the amino acid sequence of SEQ ID NO:10. The polypeptide may comprise a T cell receptor beta (TCR-b) variable region. In some aspects, the polypeptide comprises a TCR-b variable and constant region. The polypeptide may comprise or further comprise a signal peptide. The signal peptide may comprise an amino acid sequence having at least 80% identity to SEQ ID NO:11. In some aspects, the signal peptide comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:11. The signal peptide comprises the amino acid sequence of SEQ ID NO:11. In some aspects, the variable region may comprise a CDR1, CDR2, and/or CDR3.

The TCR may comprise a TCR-a polypeptide comprising a variable region comprising CDR1, CDR2, and CDR3 and a TCR-b polypeptide comprising a variable region comprising CDR1, CDR2, and CDR3. The TCR-a polypeptide may comprise a CDR1 with at least 80% sequence identity to SEQ ID NO:6 and/or the TCR-b polypeptide may comprise a CDR1 with at least 80% sequence identity to SEQ ID NO:12. The TCR-a polypeptide may comprise a CDR1 with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:6 and/or the TCR-b polypeptide may comprise a CDR1 with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:12. The TCR-a polypeptide may comprise a CDR1 comprising the amino acid sequence of SEQ ID NO:6 and the TCR-b polypeptide may comprise a CDR1 comprising the amino acid sequence of SEQ ID NO:12. In some aspects, the TCR-a polypeptide comprises a CDR2 with at least 80% sequence identity to SEQ ID NO:7 and the TCR-b polypeptide comprises a CDR2 with at least 80% sequence identity to SEQ ID NO:13. In some aspects, the TCR-a polypeptide comprises a CDR2 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:7 and the TCR-b polypeptide comprises a CDR2 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:13. In some aspects, the TCR-a polypeptide comprises a CDR2 comprising the amino acid sequence of SEQ ID NO:7 and the TCR-b polypeptide comprises a CDR2 comprising the amino acid sequence of SEQ ID NO:13. The CDR1, CDR2, and CDR3 of the TCR-a polypeptide may comprise the amino acid sequence of SEQ ID NO: 6, 7, and 8, respectively and wherein the CDR1, CDR3, and CDR3 of the TCR-b polypeptide may comprise the amino acid sequence of SEQ ID NO:12, 13, and 14, respectively. In some aspects, the TCR-a variable region comprises an amino acid sequence with at least 70% sequence identity to SEQ ID NO:4 and the TCR-b variable region comprises an amino acid sequence with at least 70% sequence identity to SEQ ID NO:10. In some aspects, the TCR-a variable region comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:4 and the TCR-b variable region comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:10. In some aspects, the TCR-a polypeptide comprises an amino acid sequence having at least 70% sequence identity to SEQ ID NO:3 and the TCR-b polypeptide comprises an amino acid sequence having at least 70% sequence identity to SEQ ID NO:9. In some aspects, the TCR-a polypeptide comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:3 and the TCR-b polypeptide comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:9. The TCR-a and/or TCR-b polypeptide may comprise a signal peptide. The signal peptide may comprise SEQ ID NO:5 or 11. In some aspects, the signal peptide comprises an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:5 or 11.

The TCR may comprise a modification or is chimeric. The variable region of the TCR may be fused to a TCR constant region that is different from the constant region of the cloned TCR that specifically binds to a peptide of the disclosure.

The TCR-a polypeptide and TCR-b polypeptide may be operably linked. The term "operably linked" can refer to a covalent linkage, such as a peptide bond (e.g. the two elements are polypeptides and are on the same polypeptide), or a non-covalent linkage, such as Van der Waals force (e.g. two polypeptides that have a certain degree of specific binding affinity for each other). The TCR-a polypeptide and TCR-b polypeptide are operably linked through a peptide bond. The TCR-a polypeptide and TCR-b polypeptide are on the same polypeptide and wherein the TCR-b is amino-proximal to the TCR-a. The polypeptide may be further defined as a single-chain TCR. The TCR-a polypeptide and TCR-b polypeptide may be on the same polypeptide and wherein the TCR-a is amino-proximal to the TCR-b. The TCR may comprise a linker between the TCR-a and TCR-b polypeptide. The linker may comprise glycine and serine residues. Further linkers useful in the polypeptides and TCRs of the disclosure are described herein. A first region is carboxy-proximal to a second region when the first region is attached to the carboxy terminus of the second region. There may be further intervening amino acid residues between the first and second regions. Thus, the regions need not be immediately adjacent, unless specifically specified as not having intervening amino acid residues. The term "amino-proximal" is similarly defined in that a first region is amino-proximal to a second region when the first region is attached to the amino terminus of the second region. Similarly, there may be further intervening amino acid residues between the first and second regions unless stated otherwise.

A CDR may also comprise 1, 2, 3, 4, 5, 6, 7, 8, 9, 10, 11, 12, 13, 14, 15, 16, 16, 18, 19, 20, 21, 22, 23, or more contiguous amino acid residues (or any range derivable therein) flanking one or both sides of a particular CDR sequence; therefore, there may be one or more additional amino acids at the N-terminal or C-terminal end of a particular CDR sequence, such as those shown in SEQ ID NOS:6-8 and 12-14.

The TCR or fusion protein may be conjugated to a detection or therapeutic agent. The agent may comprise a fluorescent molecule, radiative molecule, or toxin. In some aspects, the TCR or fusion protein is conjugated to an agent described herein.

The disclosure also provides for a nucleic acid encoding a TCR-a polypeptide comprising a CDR3 comprising an amino acid sequence with at least 80% sequence identity to AVRADRGSTLGRLY (SEQ ID NO:8) and/or a TCR-b polypeptide comprising a CDR3 comprising an amino acid sequence with at least 80% sequence identity to ASSVDGGASGEQF (SEQ ID NO:14). In some aspects, the nucleic acid encodes a TCR-a polypeptide comprising a CDR3 comprising an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:8 and/or the TCR-b polypeptide comprises a CDR3 comprising an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:14. The nucleic acid may encode for a TCR-a polypeptide comprising a CDR1, CDR2, and CDR3 and/or a TCR-b polypeptide comprising a CDR1, CDR2, and CDR3. The nucleic acid may encode for a TCR-a comprising a CDR1 with at least 80% sequence identity to SEQ ID NO:6 and/or a TCR-b comprising a CDR1 with at least 80% sequence identity to SEQ ID NO:12. In some aspects, the nucleic acid encodes for a TCR-a comprising a CDR1 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:6 and/or a TCR-b comprising a CDR1 having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:12. In some aspects, the nucleic acid encodes for a TCR-a comprising a CDR2 with at least 80% sequence identity to SEQ ID NO:7 and/or a TCR-b comprising a CDR2 with at least 80% sequence identity to SEQ ID NO:13. In some aspects, the nucleic acid encodes for a TCR-a comprising a CDR2 with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:7 and/or a TCR-b comprising a CDR2 with at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:13. In some aspects, the nucleic acid encodes a TCR-a variable region comprising an amino acid sequence with at least 70% sequence identity to SEQ ID NO:4 and/or a TCR-b variable region comprising an amino acid sequence with at least 70% sequence identity to SEQ ID NO:10. In some aspects, the nucleic acid encodes a TCR-a variable region comprising an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:4 and/or a TCR-b variable region comprising an amino acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:10. In some aspects, the nucleic acid encodes a TCR-a polypeptide chain comprises the amino acid sequence of SEQ ID NO:4 and/or a TCR-b chain comprising an amino acid of SEQ ID NO:10. In some aspects, the nucleic acid comprises SEQ ID NO:1 and/or SEQ ID NO:2. In some aspects, the nucleic acid comprises a nucleic acid sequence having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:1 and/or having or having at least 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:2.

The nucleic acid may comprise a TCR-a (TRA) and TCR-b (TRB) gene. The nucleic acid may be polycistronic. The nucleic acid may also comprise an internal ribosome entry site (IRES) or a P2A linker. The nucleic acid may comprise a cDNA encoding the TCR-a and/or TCR-b genes. The nucleic acid may encode or further encode for a polypeptide comprising a CD3 binding region. In some aspects, the CD3 binding region comprises a CD3-specific fragment antigen binding (Fab), single chain variable fragment (scFv), single domain antibody, or single chain antibody.

The vector may comprise both of the TCR-a and TCR-b genes. The vector may comprise a promoter that directs the expression of the nucleic acid. The promoter may comprise a murine stem cell virus (MSCV) promoter. In some aspects, the cell comprises a stem cell, a progenitor cell, an immune cell, or a natural killer (NK) cell. In some aspects, the cell comprises a hematopoietic stem or progenitor cell, a T cell, a cell differentiated from mesenchymal stem cells (MSCs) or an induced pluripotent stem cell (iPSC). The cell may be isolated or derived from peripheral blood mononuclear cell (PBMCs). In some aspects, the T cell comprises a cytotoxic T lymphocyte (CTL), a CD8+ T cell, a CD4+ T cell, an invariant NK T (iNKT) cell, a gamma-delta T cell, a NKT cell, or a regulatory T cell. In some aspects, the cell is isolated from a cancer patient. In some aspects, the cell is isolated from a non-cancerous patient. In some aspects, the cell is isolated from a healthy patient. The cell may be frozen or may have never been frozen. The cell may be in cell culture. In some aspects, the cell lacks endogenous expression of TCR genes. In some aspects, the cell further comprises a chimeric antigen receptor (CAR).

In some aspects, the composition has been determined to be serum-free, *Mycoplasma*-free, endotoxin-free, and/or sterile. The method may comprise or further comprise culturing the cell in media, incubating the cell at conditions that allow for the division of the cell, screening the cell, and/or freezing the cell.

In some aspects, the subject has been diagnosed with cancer, such as a cancer described herein. The cancer may comprise a solid tumor. The subject may be one that has been previously been treated for the cancer. The subject may be one that has been determined to be resistant to the previous treatment. The method may comprise or further comprise the administration of an additional therapy. The cancer may comprise glioma, thyroid, lung, colorectal, head and neck, stomach, liver, pancreatic, renal, urothelial, prostate, testis, breast, glioblastoma, cervical, endometrial, ovarian, or melanoma cancer. The cancer may comprise renal cancer. The cancer may comprise glioblastoma. The cancer may comprise a COL6A3+ cancer. The subject or patient may be one that has been determined to have COL6A3+ cancer cells or cancel cells that are positive for the epitope of SEQ ID NO:15. In some aspects, the cancer is a COL6A3+ overexpressing cancer, such as overexpression compared to a non-cancerous subject. The subject or patient may be one that has been determined to have COL6A3 overexpression in a biological sample. The biological sample may comprise cancer cells or a biopsy. The subject may be a mammal. In some aspects, the subject comprises a laboratory test animal, such as a mouse, rat, rabbit, dog, cat, horse, or pig. In some aspects, the subject is a human. In some aspects, the subject has been determined to be HLA-A2 and/or HLA-A*0201 positive.

The compositions of the disclosure may be formulated as a vaccine. The compositions and methods of the disclosure provide for prophylactic therapies to prevent cancer. The compositions and methods of the disclosure provide for therapeutic therapies to treat existing cancers, such as for the treatment of patients with cancer. The composition may comprise or further comprise an adjuvant. Adjuvants are known in the art and include, for example, TLR agonists and aluminum salts.

The methods of the disclosure may comprise or further comprise screening the cell for one or more cellular properties, such as for TCR expression, incorporation of nucleic acids encoding TCR genes, or for immunogenic properties, such as binding of the TCR to a cancer antigen such as COL6A3 or a peptide of SEQ ID NO:15.

The method may comprise or further comprise administering a cell or a composition comprising a cell and wherein the cell comprises an autologous cell. In some aspects, the cell comprises a non-autologous cell. The cell may also be allogenic or xenogenic.

Treatment" or Treating may refer to any treatment of a disease in a mammal, including: (i) preventing the disease, that is, causing the clinical symptoms of the disease not to develop by administration of a protective composition prior to the induction of the disease; (ii) suppressing the disease, that is, causing the clinical symptoms of the disease not to develop by administration of a protective composition after the inductive event but prior to the clinical appearance or reappearance of the disease; (iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance. In some aspects, the treatment may exclude prevention of the disease.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment or aspect.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments and aspects described in the context of the term "comprising" may also be implemented in the context of the term "consisting of" or "consisting essentially of."

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Use of the one or more sequences or compositions may be employed based on any of the methods described herein. Other embodiments are discussed throughout this application. Any embodiment or aspect discussed with respect to one aspect of the disclosure applies to other aspects of the disclosure as well and vice versa.

It is specifically contemplated that any limitation discussed with respect to one embodiment or aspect of the invention may apply to any other embodiment or aspect of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments and aspects of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Epitope recognition affinity assay of COL6A3-642 specific CTL cell lines. T2 cells pulsed with various concentrations of COL6A3-642 peptide were used as targets. The lysis ability of different COL6A3-642 specific CTL cell lines was detected with Cr51 release assay (CRA). The effector to target (E:T) ratio is 20:1.

FIG. 3A-C. Functional validation of COL6A3-642 specific CTL cell lines. Different tumor targets U87MG, T98G, LN-18 and M059K were co-cultured with different COL6A3-642 specific CTL cell lines. The lysis ability of COL6A3-642 CTL cell lines were detected with Cr51 release assay (CRA). The effector to target (E:T) ratio is from 40:1 to 1.25:1. Both C4 and G4 CTL cell lines could effectively lysis the positive targets T98G and LN-18, but not for the negative target M095K.

DETAILED DESCRIPTION OF THE INVENTION

Figure 1:
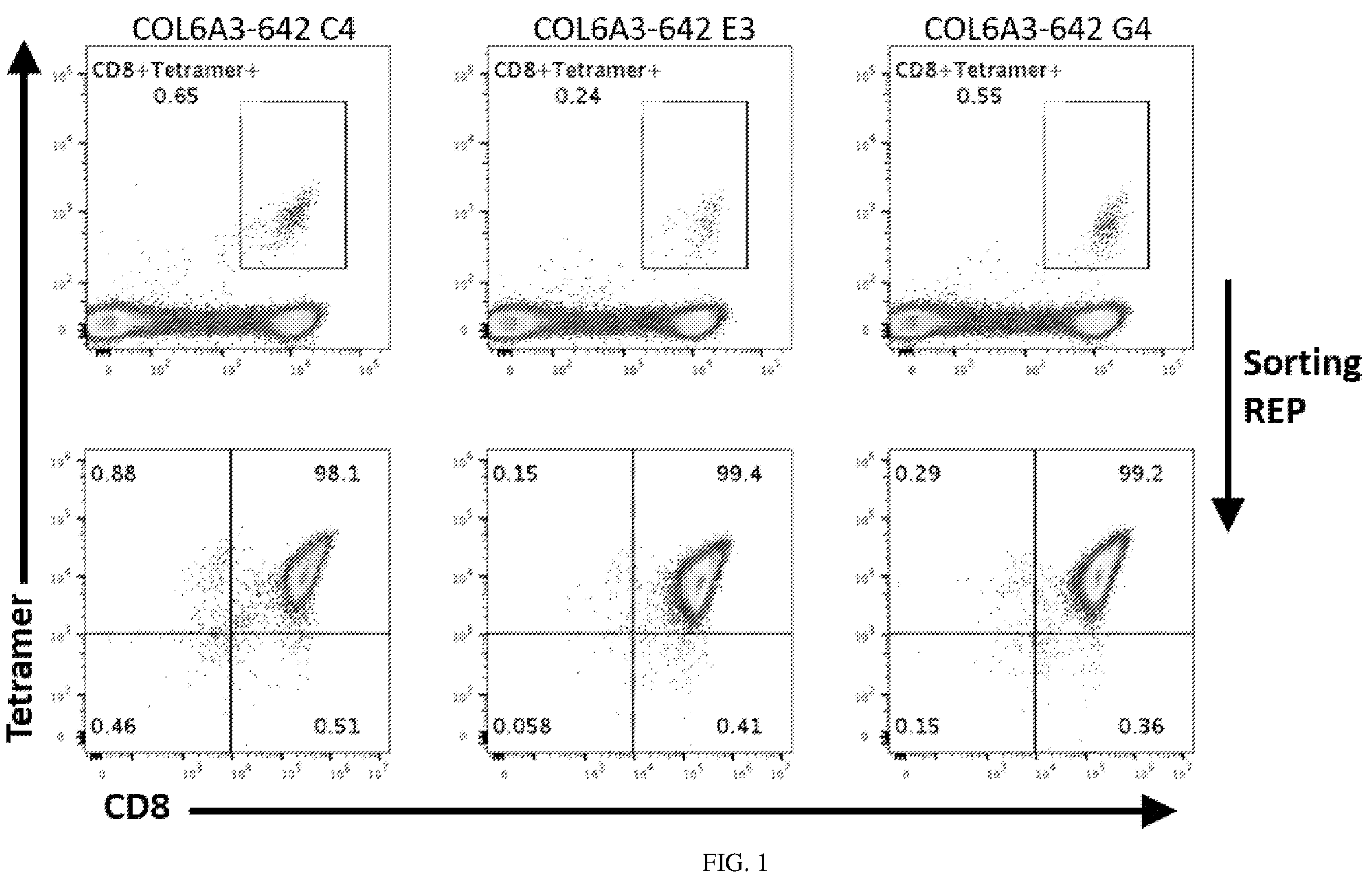
FIG. 1. COL6A3-642 peptide specific CTL generation. Mature dendritic cells (mDCs) derived from HLA-A0201+ healthy donor's PBMC were pulsed with COL6A3-642 peptide and then co-cultured with autologous T cells. After two rounds of stimulation, the CD8+/tetramer+ cell population were appeared and sorted out for further expansion. After expanding with rapid expansion protocol (REP), high purity of CD8+/tetramer CTL cells were observed. Tree COL6A3-642 specific CTL cell lines, C4, E3, G4, were generated.

The current disclosure provides a T-cell receptor (TCR) which recognizes a HLA-A2 restricted epitope from tumor antigen COL6A3 having the amino acid sequence FLLDGSANV (SEQ ID NO:15). The present disclosure also provides a nucleotide sequence encoding this TCR, an expression vector comprising this nucleotide sequence which can be used to modify cells, such as peripheral blood mononuclear cells, to generate the COL6A3-specific T cells. The present disclosure also provides the use of COL6A3-specific T cells for adoptive immunotherapy for HLA-A2 positive cancer patients whose malignant cells express COL6A3 antigen.

I. Engineered T Cell Receptors

T-cell receptors comprise two different polypeptide chains, termed the T-cell receptor α (TCRα) and β (TCRβ) chains, linked by a disulfide bond. These α:β heterodimers are very similar in structure to the Fab fragment of an immunoglobulin molecule, and they account for antigen recognition by most T cells. A minority of T cells bear an alternative, but structurally similar, receptor made up of a different pair of polypeptide chains designated γ and δ. Both types of T-cell receptor differ from the membrane-bound immunoglobulin that serves as the B-cell receptor: a T-cell receptor has only one antigen-binding site, whereas a B-cell receptor has two, and T-cell receptors are never secreted, whereas immunoglobulin can be secreted as antibody.

Both chains of the T-cell receptor have an amino-terminal variable (V) region with homology to an immunoglobulin V domain, a constant (C) region with homology to an immunoglobulin C domain, and a short hinge region containing a cysteine residue that forms the interchain disulfide bond. Each chain spans the lipid bilayer by a hydrophobic transmembrane domain, and ends in a short cytoplasmic tail.

The three-dimensional structure of the T-cell receptor has been determined. The structure is indeed similar to that of an antibody Fab fragment, as was suspected from earlier studies on the genes that encoded it. The T-cell receptor chains fold in much the same way as those of a Fab fragment, although the final structure appears a little shorter and wider. There are, however, some distinct differences between T-cell receptors and Fab fragments. The most striking difference is in the Cα domain, where the fold is unlike that of any other immunoglobulin-like domain. The half of the domain that is juxtaposed with the Cβ domain forms a β sheet similar to that found in other immunoglobulin-like domains, but the other half of the domain is formed of loosely packed strands and a short segment of α helix. The intramolecular disulfide bond, which in immunoglobulin-like domains normally joins two β strands, in a Cα domain joins a β strand to this segment of α helix.

There are also differences in the way in which the domains interact. The interface between the V and C domains of both T-cell receptor chains is more extensive than in antibodies, which may make the hinge joint between the domains less flexible. And the interaction between the Cα and Cβ domains is distinctive in being assisted by carbohydrate, with a sugar group from the Cα domain making a number of hydrogen bonds to the Cβ domain. Finally, a comparison of the variable binding sites shows that, although the complementarity-determining region (CDR) loops align fairly closely with those of antibody molecules, there is some displacement relative to those of the antibody molecule. This displacement is particularly marked in the Vα CDR2 loop, which is oriented at roughly right angles to the equivalent loop in antibody V domains, as a result of a shift in the β strand that anchors one end of the loop from one face of the domain to the other. A strand displacement also causes a change in the orientation of the Vβ CDR2 loop in two of the seven Vβ domains whose structures are known. As yet, the crystallographic structures of seven T-cell receptors have been solved to this level of resolution.

Aspects of the disclosure relate to engineered T cell receptors. The term "engineered" refers to T cell receptors that have TCR variable regions grafted onto TCR constant regions to make a chimeric polypeptide that binds to peptides and antigens of the disclosure. In certain aspects, the TCR comprises intervening sequences that are used for cloning, enhanced expression, detection, or for therapeutic control of the construct, but are not present in endogenous TCRs, such as multiple cloning sites, linker, hinge sequences, modified hinge sequences, modified transmembrane sequences, a detection polypeptide or molecule, or therapeutic controls that may allow for selection or screening of cells comprising the TCR.

In some aspects, the TCR comprises non-TCR sequences. Accordingly, certain aspects relate to TCRs with sequences that are not from a TCR gene. In some aspects, the TCR is chimeric, in that it contains sequences normally found in a TCR gene, but contains sequences from at least two TCR genes that are not necessarily found together in nature.

In some aspects the engineered TCRs of the disclosure comprise a variable as shown below:

| Description | Sequence | SEQ ID NO: |
|---|---|---|
| COL6A3-642 C4 TCR (TRAV1-2*01F-TRBV9*01F)-alpha chain | ATGTGGGGAGTTTTCCTTCTTTATGTTTCCATGAAGAT GGGAGGCACTACAGGACAAAACATTGACCAGCCCAC TGAGATGACAGCTACGGAAGGTGCCATTGTCCAGAT CAACTGCACGTACCAGACATCTGGGTTCAACGGGCTG TTCTGGTACCAGCAACATGCTGGCGAAGCACCCACAT TTCTGTCTTACAATGTTCTGGATGGTTTGGAGGAGAA AGGTCGTTTTTCTTCATTCCTTAGTCGGTCTAAAGGGT ACAGTTACCTCCTTTTGAAGGAGCTCCAGATGAAAGA CTCTGCCTCTTACCTCTGTGCTGTGAGGGCCGACAGA GGCTCAACCCTGGGGAGGCTATACTTTGGAAGAGGA ACTCAGTTGACTGTCTGGCCTGATATCCAGAACCCTG ACCCTGCCGTGTACCAGCTGAGAGACTCTAAATCCAG TGACAAGTCTGTCTGCCTATTCACCGATTTTGATTCTC AAACAAATGTGTCACAAAGTAAGGATTCTGATGTGT ATATCACAGACAAAACTGTGCTAGACATGAGGTCTAT GGACTTCAAGAGCAACAGTGCTGTGGCCTGGAGCAA CAAATCTGACTTTGCATGTGCAAACGCCTTCAACAAC AGCATTATTCCAGAAGACACCTTCTTCCCCAGCCCAG AAAGTTCCTGTGATGTCAAGCTGGTCGAGAAAAGCTT TGAAACAGATACGAACCTAAACTTTCAAAACCTGTCA GTGATTGGGTTCCGAATCCTCCTCCTGAAAGTGGCCG GGTTTAATCTGCTCATGACGCTGCGGCTGTGGTCCAG CTAA | 1 |
| COL6A3-642 C4 TCR (TRAV1-2*01F-TRBV9*01F)-beta chain | ATGGGCTTCAGGCTCCTCTGCTGTGTGGCCTTTTGTCT CCTGGGAGCAGGCCCAGTGGATTCTGGAGTCACACA AACCCCAAAGCACCTGATCACAGCAACTGGACAGCG AGTGACGCTGAGATGCTCCCCTAGGTCTGGAGACCTC TCTGTGTACTGGTACCAACAGAGCCTGGACCAGGGCC TCCAGTTCCTCATTCAGTATTATAATGGAGAAGAGAG AGCAAAAGGAAACATTCTTGAACGATTCTCCGCACA ACAGTTCCCTGACTTGCACTCTGAACTAAACCTGAGC | 2 |

-continued

| Description | Sequence | SEQ ID NO: |
|---|---|---|
| | TCTCTGGAGCTGGGGGACTCAGCTTTGTATTTCTGTG CCAGCAGCGTAGACGGGGGGGCCTCGGGGGAGCAGT TCTTCGGGCCAGGGACACGGCTCACCGTGCTAGAGG ACCTGAAAAACGTGTTCCCACCCGAGGTCGCTGTGTT TGAGCCATCAGAAGCAGAGATCTCCCACACCCAAAA GGCCACACTGGTGTGCCTGGCCACAGGCTTCTTCCCT GACCACGTGGAGCTGAGCTGGTGGGTGAATGGGAAG GAGGTGCACAGTGGGGTCAGCACGGACCCGCAGCCC CTCAAGGAGCAGCCCGCCCTCAATGACTCCAGATACT GCCTGAGCAGCCGCCTGAGGGTCTCGGCCACCTTCTG GCAGAACCCCCGCAACCACTTCCGCTGTCAAGTCCAG TTCTACGGGCTCTCGGAGAATGACGAGTGGACCCAG GATAGGGCCAAACCCGTCACCCAGATCGTCAGCGCC GAGGCCTGGGGTAGAGCAGACTGTGGCTTTACCTCG GTGTCCTACCAGCAAGGGGTCCTGTCTGCCACCATCC TCTATGAGATCCTGCTAGGGAAGGCCACCCTGTATGC TGTGCTGGTCAGCGCCCTTGTGTTGATGGCCATGGTC AAGAGAAAGGATTTCTAA | |
| COL6A3-642 C4 TCR (TRAV1-2*01F-TRBV9*01F)-alpha chain | MWGVFLLYVSMKMGGTTGQNIDQPTEMTATEGAIVQI NCTYQTSGFNGLFWYQQHAGEAPTFLSYNVLDGLEEK GRFSSFLSRSKGYSYLLLKELQMKDSASYLCAVRADRG STLGRLYFGRGTQLTVWPDIQNPDPAVYQLRDSKSSDK SVCLFTDFDSQTNVSQSKDSDVYITDKTVLDMRSMDFK SNSAVAWSNKSDFACANAFNNSIIPEDTFFPSPESSCDV KLVEKSFETDTNLNFQNLSVIGFRILLLKVAGFNLLMTL RLWSS | 3 |
| alpha chain Variable region | GQNIDQPTEMTATEGAIVQINCTYQTSGFNGLFWYQQH AGEAPTFLSYNVLDGLEEKGRFSSFLSRSKGYSYLLLKE LQMKDSASYLCAVRADRGSTLGRLYFGRGTQLTVWPD | 4 |
| Signal Peptide | MWGVFLLYVSMKMGGTT | 5 |
| alpha chain CDR1 | TSGFNG | 6 |
| alpha chain CDR2 | NVLDGL | 7 |
| alpha chain CDR3 | AVRADRGSTLGRLY | 8 |
| COL6A3-642 C4 TCR (TRAV1-2*01F-TRBV9*01F)-beta chain | MGFRLLCCVAFCLLGAGPVDSGVTQTPKHLITATGQRV TLRCSPRSGDLSVYWYQQSLDQGLQFLIQYYNGEERAK GNILERFSAQQFPDLHSELNLSSLELGDSALYFCASSVD GGASGEQFFGPGTRLTVLEDLKNVFPPEVAVFEPSEAEI SHTQKATLVCLATGFFPDHVELSWWVNGKEVHSGVST DPQPLKEQPALNDSRYCLSSRLRVSATFWQNPRNHFRC QVQFYGLSENDEWTQDRAKPVTQIVSAEAWGRADCGF TSVSYQQGVLSATILYEILLGKATLYAVLVSALVLMAM VKRKDF | 9 |
| beta chain Variable region | DSGVTQTPKHLITATGQRVTLRCSPRSGDLSVYWYQQS LDQGLQFLIQYYNGEERAKGNILERFSAQQFPDLHSELN LSSLELGDSALYFCASSVDGGASGEQFFGPGTRLTVL | 10 |
| Signal Peptide | MGFRLLCCVAFCLLGAGPV | 11 |
| beta chain CDR1 | SGDLS | 12 |
| beta chain CDR2 | YYNGEE | 13 |
| beta chain CDR3 | ASSVDGGASGEQF | 14 |
| COL6A3 tumor antigen | FLLDGSANV | 15 |

The following table relates to features of the TCR-a aspects:

| Result summary: | Productive TRA rearranged sequence (no stop codon and in-frame junction) | | |
|---|---|---|---|
| V-GENE and allele | Homsap TRAV1-2*01 F | score = 1315 | identity = 100.00% (264/264 nt) |
| J-GENE and allele | Homsap TRAJ18*01 F | score = 330 | identity = 100.00% (66/66 nt) |
| FR-IMGT lengths, CDR-IMGT lengths and AA JUNCTION | [25.17. 34.11] | [6.6.14] | CAVRADRGSTLGRLYF (SEQ ID NO: 16) |

The following table relates to features of the TCR-b aspects:

| Result summary: | Productive TRB rearranged sequence (no stop codon and in-frame junction) | | |
|---|---|---|---|
| V-GENE and allele | Homsap TRBV9*01 F | score = 1360 | identity = 100.00% (273/27 3nt) |
| J-GENE and allele | Homsap TRBJ2-1*01 F | score = 187 | identity = 86.00% (43/50 nt) |
| D-GENE and allele by IMGT/ Junction Analysis | Homsap TRBD2*01 F | D-REGION is in reading frame 1 | |
| FR-IMGT lengths, CDR-IMGT lengths and AA JUNCTION | [26.17. 37.10] | [5.6.13] | CASSVDGG ASGEQFF (SEQ ID NO: 17) |

II. Proteinaceous Compositions

As used herein, a "protein" "peptide" or "polypeptide" refers to a molecule comprising at least five amino acid residues. As used herein, the term "wild-type" refers to the endogenous version of a molecule that occurs naturally in an organism. In some aspects, wild-type versions of a protein or polypeptide are employed, however, in many aspects of the disclosure, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some aspects, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Where a protein is specifically mentioned herein, it is in general a reference to a native (wild-type) or recombinant (modified) protein or, optionally, a protein in which any signal sequence has been removed. The protein may be isolated directly from the organism of which it is native, produced by recombinant DNA/exogenous expression methods, or produced by solid-phase peptide synthesis (SPPS) or other in vitro methods. In particular aspects, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

In certain aspects the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 1000, 1200, 1400, 1600, 1800, or 2000 amino acid residues or nucleic acid residues or greater, and any range derivable therein, or derivative of a corresponding amino sequence described or referenced herein. It is contemplated that polypeptides may be mutated by truncation, rendering them shorter than their corresponding wild-type form, also, they might be altered by fusing or conjugating a heterologous protein or polypeptide sequence with a particular function (e.g., for targeting or localization, for enhanced immunogenicity, for purification purposes, etc.).

The polypeptides, proteins, or polynucleotides encoding such polypeptides or proteins of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous to at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID NOS:1-17. In specific aspects, the peptide or polypeptide is or is based on a human sequence. In certain aspects, the peptide or polypeptide is not naturally occurring and/or is in a combination of peptides or polypeptides.

In some aspects, the protein, polypeptide, or nucleic acid may comprise amino acids or nucleotides 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 (or any derivable range therein) of SEQ ID NOS:1-17.

In some aspects, the protein, polypeptide, or nucleic acid may comprise amino acids or nucleotides 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 (or any derivable range therein) of SEQ ID NOS:1-17 and have or have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) sequence identity to one of SEQ ID NOS:1-17.

In some aspects, the protein, polypeptide, or nucleic acid may comprise, comprise at least, or comprise at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 (or any derivable range therein) contiguous amino acids or nucleic acids of SEQ ID NOS: 1-17.

In some aspects, the polypeptide, protein, or nucleic acid may comprise at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 (or any derivable range therein) contiguous amino acids of SEQ ID NOS:1-17 that are at least, at most, or exactly 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous to one of SEQ ID NOS:1-17.

In some aspects there is a nucleic acid molecule or polypeptide starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, or 950 of any of SEQ ID NOS:1-17 and comprising at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, or 950 (or any derivable range therein) contiguous amino acids or nucleotides of any of SEQ ID NOS:1-17.

The nucleotide as well as the protein, polypeptide, and peptide sequences for various genes have been previously disclosed, and may be found in the recognized computerized databases. Two commonly used databases are the National Center for Biotechnology Information's Genbank and GenPept databases (on the World Wide Web at ncbi.nlm.nih.gov/) and The Universal Protein Resource (UniProt; on the World Wide Web at uniprot.org). The coding regions for these genes may be amplified and/or expressed using the techniques disclosed herein or as would be known to those of ordinary skill in the art.

It is contemplated that in compositions of the disclosure, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein).

The following is a discussion of changing the amino acid subunits of a protein to create an equivalent, or even improved, second-generation variant polypeptide or peptide. For example, certain amino acids may be substituted for other amino acids in a protein or polypeptide sequence with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence and in its corresponding DNA coding sequence, and nevertheless produce a protein with similar or desirable properties. It is thus contemplated by the inventors that various changes may be made in the DNA sequences of genes which encode proteins without appreciable loss of their biological utility or activity.

The term "functionally equivalent codon" is used herein to refer to codons that encode the same amino acid, such as the six different codons for arginine. Also considered are "neutral substitutions" or "neutral mutations" which refers to a change in the codon or codons that encode biologically equivalent amino acids.

Amino acid sequence variants of the disclosure can be substitutional, insertional, or deletion variants. A variation in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the protein or polypeptide, as compared to wild-type (or any range derivable therein). A variant can comprise an amino acid sequence that is at least 50%, 60%, 70%, 80%, or 90%, including all values and ranges there between, identical to any sequence provided or referenced herein. A variant can include 2, 3, 4, 5, 6, 7, 8, 9, 10, 11, 12, 13, 14, 15, 16, 17, 18, 19, 20, or more substitute amino acids.

It also will be understood that amino acid and nucleic acid sequences may include additional residues, such as additional N- or C-terminal amino acids, or 5' or 3' sequences, respectively, and yet still be essentially identical as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Deletion variants typically lack one or more residues of the native or wild type protein. Individual residues can be deleted or a number of contiguous amino acids can be deleted. A stop codon may be introduced (by substitution or insertion) into an encoding nucleic acid sequence to generate a truncated protein.

Insertional mutants typically involve the addition of amino acid residues at a non-terminal point in the polypeptide. This may include the insertion of one or more amino acid residues. Terminal additions may also be generated and can include fusion proteins which are multimers or concatemers of one or more peptides or polypeptides described or referenced herein.

Substitutional variants typically contain the exchange of one amino acid for another at one or more sites within the protein or polypeptide, and may be designed to modulate one or more properties of the polypeptide, with or without the loss of other functions or properties. Substitutions may be conservative, that is, one amino acid is replaced with one of similar chemical properties. "Conservative amino acid substitutions" may involve exchange of a member of one amino acid class with another member of the same class. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Conservative amino acid substitutions may encompass non-naturally occurring amino acid residues, which are typically incorporated by chemical peptide synthesis rather than by synthesis in biological systems. These include peptidomimetics or other reversed or inverted forms of amino acid moieties.

Alternatively, substitutions may be "non-conservative", such that a function or activity of the polypeptide is affected. Non-conservative changes typically involve substituting an amino acid residue with one that is chemically dissimilar, such as a polar or charged amino acid for a nonpolar or uncharged amino acid, and vice versa. Non-conservative substitutions may involve the exchange of a member of one of the amino acid classes for a member from another class.

One skilled in the art can determine suitable variants of polypeptides as set forth herein using well-known techniques. One skilled in the art may identify suitable areas of the molecule that may be changed without destroying activity by targeting regions not believed to be important for activity. The skilled artisan will also be able to identify amino acid residues and portions of the molecules that are conserved among similar proteins or polypeptides. In further aspects, areas that may be important for biological activity or for structure may be subject to conservative amino acid substitutions without significantly altering the biological activity or without adversely affecting the protein or polypeptide structure.

In making such changes, the hydropathy index of amino acids may be considered. The hydropathy profile of a protein is calculated by assigning each amino acid a numerical value ("hydropathy index") and then repetitively averaging these values along the peptide chain. Each amino acid has been assigned a value based on its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5). The importance of the hydropathy amino acid index in conferring interactive biologic function on a protein is generally understood in the art (Kyte et al., J. Mol. Biol. 157:105-131 (1982)). It is accepted that the relative hydropathic character of the amino acid contributes to the secondary structure of the resultant protein or polypeptide, which in turn defines the interaction of the protein or polypeptide with other molecules, for example, enzymes, substrates, receptors, DNA, antibodies, antigens, and others. It is also known that certain amino acids may be substituted for other amino acids having a similar hydropathy index or score, and still retain a similar biological activity. In making changes based upon the hydropathy index, in certain aspects, the substitution of amino acids whose hydropathy indices are within ±2 is included. In some aspects of the invention, those that are within ±1 are included, and in other aspects of the invention, those within ±0.5 are included.

It also is understood in the art that the substitution of like amino acids can be effectively made based on hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. In certain aspects, the greatest local average hydrophilicity of a protein, as governed by the hydrophilicity of its adjacent amino acids, correlates with its immunogenicity and antigen binding, that is, as a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain aspects, the substitution of amino acids whose hydrophilicity values are within ±2 are included, in other aspects, those which are within ±1 are included, and in still other aspects, those within ±0.5 are included. In some instances, one may also identify epitopes from primary amino acid sequences based on hydrophilicity. These regions are also referred to as "epitopic core regions." It is understood that an amino acid can be substituted for another having a similar hydrophilicity value and still produce a biologically equivalent and immunologically equivalent protein.

Additionally, one skilled in the art can review structure-function studies identifying residues in similar polypeptides or proteins that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar proteins or polypeptides. In view of such information, one skilled in the art may predict the alignment of amino acid residues of an antibody with respect to its three-dimensional structure. One skilled in the art may choose not to make changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using standard assays for binding and/or activity, thus yielding information gathered from such routine experiments, which may allow one skilled in the art to determine the amino acid positions where further substitutions should be avoided either alone or in combination with other mutations. Various tools available to determine secondary structure can be found on the world wide web at expasy.org/proteomics/protein structure.

In some aspects of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain aspects, conservative amino acid substitutions) may be made in the naturally occurring sequence. Substitutions can be made in that portion of the antibody that lies outside the domain(s) forming intermolecular contacts. In such aspects, conservative amino acid substitutions can be used that do not substantially change the structural characteristics of the protein or polypeptide (e.g., one or more replacement amino acids that do not disrupt the secondary structure that characterizes the native antibody).

III. Nucleic Acids

In certain aspects, nucleic acid sequences can exist in a variety of instances such as: isolated segments and recombinant vectors of incorporated sequences or recombinant polynucleotides encoding one or both chains of an antibody, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing described herein. Nucleic acids that encode the epitope to which certain of the antibodies provided herein are also provided. Nucleic acids encoding fusion proteins that include these peptides are also provided. The nucleic acids can be single-stranded or double-stranded and can comprise RNA and/or DNA nucleotides and artificial variants thereof (e.g., peptide nucleic acids).

The term "polynucleotide" refers to a nucleic acid molecule that either is recombinant or has been isolated from total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

In certain aspects, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

A. Hybridization

The nucleic acids that hybridize to other nucleic acids under particular hybridization conditions. Methods for hybridizing nucleic acids are well known in the art. See, e.g., Current Protocols in Molecular Biology, John Wiley and Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C. in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequence that are at least 65%, at least 70%, at least 75%, at least 80%, at least 85%, at least 90%, at least 95%, at least 96%, at least 97%, at least 98% or at least 99% identical to each other typically remain hybridized to each other.

The parameters affecting the choice of hybridization conditions and guidance for devising suitable conditions are set forth by, for example, Sambrook, Fritsch, and Maniatis (Molecular Cloning: A Laboratory Manual, Cold Spring Harbor Laboratory Press, Cold Spring Harbor, N.Y., chapters 9 and 11 (1989); Current Protocols in Molecular Biology, Ausubel et al., eds., John Wiley and Sons, Inc., sections 2.10 and 6.3-6.4 (1995), both of which are herein incorporated by reference in their entirety for all purposes) and can be readily determined by those having ordinary skill in the art based on, for example, the length and/or base composition of the DNA.

B. Mutation

Changes can be introduced by mutation into a nucleic acid, thereby leading to changes in the amino acid sequence of a polypeptide (e.g., an antibody or antibody derivative) that it encodes. Mutations can be introduced using any technique known in the art. In one aspect, one or more particular amino acid residues are changed using, for example, a site-directed mutagenesis protocol. In another aspect, one or more randomly selected residues are changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. See, eg., Romain Studer et al., Biochem. J. 449: 581-594 (2013). For example, the mutation can quantitatively or qualitatively change the biological activity.

Examples of quantitative changes include increasing, reducing or eliminating the activity. Examples of qualitative changes include altering the antigen specificity of an antibody.

C. Probes

In another aspect, nucleic acid molecules are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion of a given polypeptide.

In another aspect, the nucleic acid molecules may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of antibodies. See, eg., Gaily Kivi et al., BMC Biotechnol. 16:2 (2016). In a preferred aspect, the nucleic acid molecules are oligonucleotides. In a more preferred aspect, the oligonucleotides are from highly variable regions of the heavy and light or alpha and beta chains of the antibody or TCR of interest. In an even more preferred aspect, the oligonucleotides encode all or part of one or more of the CDRs or TCRs.

Probes based on the desired sequence of a nucleic acid can be used to detect the nucleic acid or similar nucleic acids, for example, transcripts encoding a polypeptide of interest. The probe can comprise a label group, e.g., a radioisotope, a fluorescent compound, an enzyme, or an enzyme co-factor. Such probes can be used to identify a cell that expresses the polypeptide.

IV. Polypeptide Expression

In some aspects, there are nucleic acid molecule encoding polypeptides or peptides of the disclosure (e.g TCR genes). These may be generated by methods known in the art, e.g., isolated from B cells of mice that have been immunized and isolated, phage display, expressed in any suitable recombinant expression system and allowed to assemble to form antibody molecules or by recombinant methods.

A. Expression

The nucleic acid molecules may be used to express large quantities of polypeptides. If the nucleic acid molecules are derived from a non-human, non-transgenic animal, the nucleic acid molecules may be used for humanization of the TCR genes.

B. Vectors

In some aspects, contemplated are expression vectors comprising a nucleic acid molecule encoding a polypeptide of the desired sequence or a portion thereof (e.g., a fragment containing one or more CDRs or one or more variable region domains). Expression vectors comprising the nucleic acid molecules may encode the heavy chain, light chain, alpha chain, beta chain, or the antigen-binding portion thereof. In some aspects, expression vectors comprising nucleic acid molecules may encode fusion proteins, modified antibodies, antibody fragments, and probes thereof. In addition to control sequences that govern transcription and translation, vectors and expression vectors may contain nucleic acid sequences that serve other functions as well.

To express the polypeptides or peptides of the disclosure, DNAs encoding the polypeptides or peptides are inserted into expression vectors such that the gene area is operatively linked to transcriptional and translational control sequences. In some aspects, a vector that encodes a functionally complete human CH or CL immunoglobulin or TCR sequence with appropriate restriction sites engineered so that any variable region sequences can be easily inserted and expressed. In some aspects, a vector that encodes a functionally complete human TCR alpha or TCR beta sequence with appropriate restriction sites engineered so that any variable sequence or CDR1, CDR2, and/or CDR3 can be easily inserted and expressed. Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Such sequences and methods of using the same are well known in the art.

C. Expression Systems

Numerous expression systems exist that comprise at least a part or all of the expression vectors discussed above. Prokaryote- and/or eukaryote-based systems can be employed for use with an aspect to produce nucleic acid sequences, or their cognate polypeptides, proteins and peptides. Commercially and widely available systems include in but are not limited to bacterial, mammalian, yeast, and insect cell systems. Different host cells have characteristic and specific mechanisms for the post-translational processing and modification of proteins. Appropriate cell lines or host systems can be chosen to ensure the correct modification and processing of the foreign protein expressed. Those skilled in the art are able to express a vector to produce a nucleic acid sequence or its cognate polypeptide, protein, or peptide using an appropriate expression system.

V. Methods of Gene Transfer

Suitable methods for nucleic acid delivery to effect expression of compositions are anticipated to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Other methods include viral transduction, such as gene transfer by lentiviral or retroviral transduction.

A. Host Cells

In another aspect, contemplated are the use of host cells into which a recombinant expression vector has been introduced. Antibodies can be expressed in a variety of cell types. An expression construct encoding an antibody can be transfected into cells according to a variety of methods known in the art. Vector DNA can be introduced into prokaryotic or eukaryotic cells via conventional transformation or transfection techniques. Some vectors may employ control sequences that allow it to be replicated and/or expressed in both prokaryotic and eukaryotic cells. In certain aspects, the antibody expression construct can be placed under control of a promoter that is linked to T-cell activation, such as one that is controlled by NFAT-1 or NF-κB, both of which are transcription factors that can be activated upon T-cell activation. Control of antibody expression allows T cells, such as tumor-targeting T cells, to sense their surroundings and perform real-time modulation of cytokine signaling, both in the T cells themselves and in surrounding endogenous immune cells. One of skill in the art would understand the conditions under which to incubate host cells to maintain them and to permit replication of a vector. Also understood and known are techniques and conditions that would allow large-scale production of vectors, as well as production of the nucleic acids encoded by vectors and their cognate polypeptides, proteins, or peptides.

For stable transfection of mammalian cells, it is known, depending upon the expression vector and transfection technique used, only a small fraction of cells may integrate the foreign DNA into their genome. In order to identify and select these integrants, a selectable marker (e.g., for resistance to antibiotics) is generally introduced into the host cells along with the gene of interest. Cells stably transfected with the introduced nucleic acid can be identified by drug selection (e.g., cells that have incorporated the selectable marker gene will survive, while the other cells die), among other methods known in the arts.

B. Isolation

The nucleic acid molecule encoding either or both of the entire heavy, light, alpha, and beta chains of an antibody or TCR, or the variable regions thereof may be obtained from any source that produces antibodies. Methods of isolating mRNA encoding an antibody are well known in the art. See e.g., Sambrook et al., supra. The sequences of human heavy and light chain constant region genes are also known in the art. See, e.g., Kabat et al., 1991, supra. Nucleic acid molecules encoding the full-length heavy and/or light chains may then be expressed in a cell into which they have been introduced and the antibody isolated.

VI. Additional Therapies

A. Immunotherapy

In some aspects, the methods comprise administration of an additional therapy. In some aspects, the additional therapy comprises a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies are known in the art, and some are described below.

1. Checkpoint Inhibitors and Combination Treatment

Aspects of the disclosure may include administration of immune checkpoint inhibitors, which are further described below.

a. PD-1, PDL1, and PDL2 Inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for "PD-1" include CD279 and SLEB2. Alternative names for "PDL1" include B7-H1, B7-4, CD274, and B7-H. Alternative names for "PDL2" include B7-DC, Btdc, and CD273. In some aspects, PD-1, PDL1, and PDL2 are human PD-1, PDL1 and PDL2.

In some aspects, the PD-1 inhibitor is a molecule that inhibits the binding of PD-1 to its ligand binding partners. In a specific aspect, the PD-1 ligand binding partners are PDL1 and/or PDL2. In another aspect, a PDL1 inhibitor is a molecule that inhibits the binding of PDL1 to its binding partners. In a specific aspect, PDL1 binding partners are PD-1 and/or B7-1. In another aspect, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some aspects, the PD-1 inhibitor is an anti-PD-1 antibody (e.g., a human antibody, a humanized antibody, or a chimeric antibody). In some aspects, the anti-PD-1 antibody is selected from the group consisting of nivolumab, pembrolizumab, and pidilizumab. In some aspects, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some aspects, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some aspects, the immune checkpoint inhibitor is a PDL1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PDL2 inhibitor such as rHIgM 12B7.

In some aspects, the inhibitor comprises the heavy and light chain CDRs or VRs of nivolumab, pembrolizumab, or pidilizumab. Accordingly, in one aspect, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another aspect, the antibody competes for binding with and/or binds to the same epitope on PD-1, PDL1, or PDL2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

b. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some aspects, the inhibitor blocks the CTLA-4 and B7-1 interaction. In some aspects, the inhibitor blocks the CTLA-4 and B7-2 interaction.

In some aspects, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10D1, MDX-010, MDX-101, and Yervoy®) or antigen binding fragments and variants thereof (see, e.g., WO 01/14424).

In some aspects, the inhibitor comprises the heavy and light chain CDRs or VRs of tremelimumab or ipilimumab. Accordingly, in one aspect, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another aspect, the antibody competes for binding with and/or binds to the same epitope on PD-1, B7-1, or B7-2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

2. Inhibition of Co-Stimulatory Molecules

In some aspects, the immunotherapy comprises an inhibitor of a co-stimulatory molecule. In some aspects, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

3. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor. Dendritic cell receptors such as TLR3, TLR7, TLR8 or CD40 have been used as antibody targets.

4. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signaling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some aspects, the CAR-T therapy targets CD19.

5. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFNα and IFNβ), type II (IFNγ) and type III (IFNλ).

Interleukins have an array of immune system effects. IL-2 is an exemplary interleukin cytokine therapy.

6. Adoptive T-Cell Therapy

Adoptive T cell therapy is a form of passive immunization by the transfusion of T-cells (adoptive cell transfer). They are found in blood and tissue and usually activate when they find foreign pathogens. Specifically they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumor death.

Multiple ways of producing and obtaining tumor targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

B. Chemotherapies

In some aspects, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as *vinca* alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some aspects, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain aspects. In some aspects, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain aspects, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable aspect, the chemotherapeutic agent may be administered in an amount effective to cause arrest or regression of the cancer in a host, when the chemotherapy is administered with the construct. In other aspects, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

C. Radiotherapy

In some aspects, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

D. Surgery

In some aspects, the additional therapy comprises surgery. Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present aspects, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months (or any range derivable therein). These treatments may be of varying dosages as well.

VII. Detection and Therapeutic Agents

In some aspects of this disclosure, it will be useful to detectably or therapeutically label the TCRs or fusion proteins of the disclosure. Methods for conjugating polypeptides to these agents are known in the art. For the purpose of illustration only, polypeptides can be labeled with a detectable moiety such as a radioactive atom, a chromophore, a fluorophore, or the like. Such labeled polypeptides can be used for diagnostic techniques, either in vivo, or in an isolated test sample or in methods described herein.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition that is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, aminocoumarin derivative (Cascade Blue™), and sulforhodamine 101 sulfonyl chloride (Texas Red®). Other suitable optical dyes are described in the Haugland, Richard P. (1996) Handbook of Fluorescent Probes and Research Chemicals (6.sup.th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/polypeptides, e.g., rhodamine/anti-rhodamine, biotin/avidin and biotin/strepavidin.

The coupling of polypeptides to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten polypeptides. See, Harlow and Lane (1988) supra.

The conjugated agents can be linked to the polypeptide directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al., 1994; Upeslacis et al., 1995; Price, 1995).

Techniques for conjugating agents to polypeptides are well known (Amon et al., 1985; Hellstrom et al., 1987; Thorpe, 1985; Baldwin et al., 1985; Thorpe et al., 1982), The polypeptides of the disclosure or antigen-binding regions thereof can be linked to another functional molecule such as ligands, cytotoxic molecules, chemotherapeutic agents, or other agents described as additional therapeutics.

VIII. Formulations and Culture of the Cells

In particular aspects, the cells of the disclosure may be specifically formulated and/or they may be cultured in a particular medium. The cells may be formulated in such a manner as to be suitable for delivery to a recipient without deleterious effects.

The medium in certain aspects can be prepared using a medium used for culturing animal cells as their basal medium, such as any of AIM V, X-VIVO-15, NeuroBasal, EGM2, TeSR, BME, BGJb, CMRL 1066, Glasgow MEM, Improved MEM Zinc Option, IMDM, Medium 199, Eagle MEM, αMEM, DMEM, Ham, RPMI-1640, and Fischer's media, as well as any combinations thereof, but the medium may not be particularly limited thereto as far as it can be used for culturing animal cells. Particularly, the medium may be xeno-free or chemically defined.

The medium can be a serum-containing or serum-free medium, or xeno-free medium. From the aspect of preventing contamination with heterogeneous animal-derived components, serum can be derived from the same animal as that of the stem cell(s). The serum-free medium refers to medium with no unprocessed or unpurified serum and accordingly, can include medium with purified blood-derived components or animal tissue-derived components (such as growth factors).

The medium may contain or may not contain any alternatives to serum. The alternatives to serum can include materials which appropriately contain albumin (such as lipid-rich albumin, bovine albumin, albumin substitutes such as recombinant albumin or a humanized albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. 98/30679, for example (incorporated herein in its entirety). Alternatively, any commercially available materials can be used for more convenience. The commercially available materials include knockout Serum Replacement (KSR), Chemically-defined Lipid concentrated (Gibco™), and Glutamax (Gibco™).

In certain aspects, the medium may comprise one, two, three, four, five, six, seven, eight, nine, ten, 11, 12, 13, 14, 15, 16, 17, 18, 19, 20 or more of the following: Vitamins such as biotin; DL Alpha Tocopherol Acetate; DL Alpha-Tocopherol; Vitamin A (acetate); proteins such as BSA (bovine serum albumin) or human albumin, fatty acid free Fraction V; Catalase; Human Recombinant Insulin; Human Transferrin; Superoxide Dismutase; Other Components such as Corticosterone; D-Galactose; Ethanolamine HCl; Glutathione (reduced); L-Carnitine HCl; Linoleic Acid; Linolenic Acid; Progesterone; Putrescine 2HCl; Sodium Selenite; and/or T3 (triodo-I-thyronine). In specific aspects, one or more of these may be explicitly excluded.

In some aspects, the medium further comprises vitamins. In some aspects, the medium comprises 1, 2, 3, 4, 5, 6, 7, 8, 9, 10, 11, 12, or 13 of the following (and any range derivable therein): biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, vitamin B12, or the medium includes combinations thereof or salts thereof. In some aspects, the medium comprises or consists essentially of biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, and vitamin B12. In some aspects, the vitamins include or consist essentially of biotin, DL alpha tocopherol acetate, DL alpha-tocopherol, vitamin A, or combinations or salts thereof. In some aspects, the medium further comprises proteins. In some aspects, the proteins comprise albumin or bovine serum albumin, a fraction of BSA, catalase, insulin, transferrin, superoxide dismutase, or combinations thereof. In some aspects, the medium further comprises one or more of the following: corticosterone, D-Galactose, ethanolamine, glutathione, L-carnitine, linoleic acid, linolenic acid, progesterone, putrescine, sodium selenite, or triodo-I-thyronine, or combinations thereof. In some aspects, the medium comprises one or more of the following: a B-27® supplement, xeno-free B-27® supplement, GS21™ supplement, or combinations thereof. In some aspects, the medium comprises or further comprises amino acids, monosaccharides, inorganic ions. In some aspects, the amino acids comprise arginine, cysteine, isoleucine, leucine, lysine, methionine, glutamine, phenylalanine, threonine, tryptophan, histidine, tyrosine, or valine, or combinations thereof. In some aspects, the inorganic ions comprise sodium, potassium, calcium, magnesium, nitrogen, or phosphorus, or combinations or salts thereof. In some aspects, the medium further comprises one or more of the following: molybdenum, vanadium, iron, zinc, selenium, copper, or manganese, or combinations thereof. In certain aspects, the medium comprises or consists essentially of one or more vitamins discussed herein and/or one or more proteins discussed herein, and/or one or more of the following: corticosterone, D-Galactose, ethanolamine, glutathione, L-carnitine, linoleic acid, linolenic acid, progesterone, putrescine, sodium selenite, or triodo-I-thyronine, a B-27® supplement, xeno-free B-27® supplement, GS21™ supplement, an amino acid (such as arginine, cysteine, isoleucine, leucine, lysine, methionine, glutamine, phenylalanine, threonine, tryptophan, histidine, tyrosine, or valine), monosaccharide, inorganic ion (such as sodium, potassium, calcium, magnesium, nitrogen, and/or phosphorus) or salts thereof, and/or molybdenum, vanadium, iron, zinc, selenium, copper, or manganese. In specific aspects, one or more of these may be explicitly excluded.

The medium can also contain one or more externally added fatty acids or lipids, amino acids (such as nonessential amino acids), vitamin(s), growth factors, cytokines, antioxidant substances, 2-mercaptoethanol, pyruvic acid, buffering agents, and/or inorganic salts. In specific aspects, one or more of these may be explicitly excluded.

One or more of the medium components may be added at a concentration of at least, at most, or about 0.1, 0.5, 1, 2, 3, 4, 5, 10, 15, 20, 25, 30, 35, 40, 45, 50, 55, 60, 65, 70, 75, 80, 85, 90, 95, 100, 150, 180, 200, 250 ng/L, ng/ml, μg/ml, mg/ml, or any range derivable therein.

In specific aspects, the cells of the disclosure are specifically formulated. They may or may not be formulated as a cell suspension. In specific cases they are formulated in a single dose form. They may be formulated for systemic or local administration. In some cases the cells are formulated for storage prior to use, and the cell formulation may comprise one or more cryopreservation agents, such as DMSO (for example, in 5% DMSO). The cell formulation may comprise albumin, including human albumin, with a specific formulation comprising 2.5% human albumin. The cells may be formulated specifically for intravenous administration; for example, they are formulated for intravenous administration over less than one hour. In particular aspects the cells are in a formulated cell suspension that is stable at room temperature for 1, 2, 3, or 4 hours or more from time of thawing.

In particular aspects, the cells of the disclosure comprise an exogenous TCR, which may be of a defined antigen specificity. In some aspects, the TCR can be selected based on absent or reduced alloreactivity to the intended recipient (examples include certain virus-specific TCRs, xeno-specific TCRs, or cancer-testis antigen-specific TCRs). In the example where the exogenous TCR is non-alloreactive, during T cell differentiation the exogenous TCR suppresses rearrangement and/or expression of endogenous TCR loci through a developmental process called allelic exclusion, resulting in T cells that express only the non-alloreactive exogenous TCR and are thus non-alloreactive. In some aspects, the choice of exogenous TCR may not necessarily be defined based on lack of alloreactivity. In some aspects, the endogenous TCR genes have been modified by genome editing so that they do not express a protein. Methods of gene editing such as methods using the CRISPR/Cas9 system are known in the art and described herein.

In some aspects, the cells of the disclosure further comprise one or more chimeric antigen receptors (CARs). Examples of tumor cell antigens to which a CAR may be directed include at least 5T4, 8H9, αvβ6 integrin, BCMA, B7-H3, B7-H6, CAIX, CA9, CD19, CD20, CD22, CD30, CD33, CD38, CD44, CD44v6, CD44v7/8, CD70, CD123, CD138, CD171, CEA, CSPG4, EGFR, EGFR family including ErbB2 (HER2), EGFRvIII, EGP2, EGP40, ERBB3, ERBB4, ErbB3/4, EPCAM, EphA2, EpCAM, folate receptor-a, FAP, FBP, fetal AchR, FRα, GD2, G250/CAIX, GD3, Glypican-3 (GPC3), Her2, IL-13Rα2, Lambda, Lewis-Y, Kappa, KDR, MAGE, MCSP, Mesothelin, Muc1, Muc16, NCAM, NKG2D Ligands, NY-ESO-1, PRAME, PSC1, PSCA, PSMA, ROR1, SP17, Survivin, TAG72, TEMs, carcinoembryonic antigen, HMW-MAA, AFP, CA-125, ETA, Tyrosinase, MAGE, laminin receptor, HPV E6, E7, BING-4, Calcium-activated chloride channel 2, Cyclin-B1, 9D7, EphA3, Telomerase, SAP-1, BAGE family, CAGE family, GAGE family, MAGE family, SAGE family, XAGE family, NY-ESO-1/LAGE-1, PAME, SSX-2, Melan-A/MART-1, GP100/pmel17, TRP-1/-2, P. polypeptide, MC1R, Prostate-specific antigen, β-catenin, BRCA1/2, CML66, Fibronectin, MART-2, TGF-βRII, or VEGF receptors (e.g., VEGFR2), for example. The CAR may be a first, second, third, or more generation CAR. The CAR may be bispecific for any two nonidentical antigens, or it may be specific for more than two nonidentical antigens.

IX. Administration of Therapeutic Compositions

The therapy provided herein may comprise administration of a combination of therapeutic agents, such as a first cancer therapy and a second cancer therapy. The therapies may be administered in any suitable manner known in the art. For example, the first and second cancer treatment may be administered sequentially (at different times) or concurrently (at the same time). In some aspects, the first and second cancer treatments are administered in a separate composition. In some aspects, the first and second cancer treatments are in the same composition.

Aspects of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic compositions of the disclosure may be administered by the same route of administration or by different routes of administration. In some aspects, the cancer therapy is administered intravenously, intramuscularly, subcutaneously, topically, orally, transdermally, intraperitoneally, intraorbitally, by implantation, by inhalation, intrathecally, intraventricularly, or intranasally. In some aspects, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some aspects, a unit dose comprises a single administrable dose.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

The cancers amenable for treatment include, but are not limited to, tumors of all types, locations, sizes, and characteristics. In some aspects, the cancer comprises a solid tumor. In some aspects, the methods relate to reducing tumor volume or treating cancers that are recurrent and/or metastatic. The methods and compositions of the disclosure are suitable for treating, for example, pancreatic cancer, colon cancer, acute myeloid leukemia, adrenocortical carcinoma, AIDS-related cancers, AIDS-related lymphoma, anal cancer, appendix cancer, astrocytoma, childhood cerebellar or cerebral basal cell carcinoma, bile duct cancer, extrahepatic bladder cancer, bone cancer, osteosarcoma/malignant fibrous histiocytoma, brainstem glioma, brain tumor, cerebellar astrocytoma brain tumor, cerebral astrocytoma/malignant glioma brain tumor, ependymoma brain tumor, medulloblastoma brain tumor, supratentorial primitive neuroectodermal tumors brain tumor, visual pathway and hypothalamic glioma, breast cancer, lymphoid cancer, bronchial adenomas/carcinoids, tracheal cancer, lung cancer, Burkitt lymphoma, carcinoid tumor, childhood carcinoid tumor, gastrointestinal carcinoma of unknown primary, central nervous system lymphoma, primary cerebellar astrocytoma, childhood cerebral astrocytoma/malignant glioma, childhood cervical cancer, childhood cancers, chronic lymphocytic leukemia, chronic myelogenous leukemia, chronic myeloproliferative disorders, cutaneous T-cell lymphoma, desmoplastic small round cell tumor, endometrial cancer, ependymoma, esophageal cancer, Ewing's, childhood extragonadal Germ cell tumor, extrahepatic bile duct cancer, eye Cancer, intraocular melanoma eye Cancer, retinoblastoma, gallbladder cancer, gastric (stomach) cancer, gastrointestinal carcinoid tumor, gastrointestinal stromal tumor (GIST), germ cell tumor: extracranial, extragonadal, or ovarian, gestational trophoblastic tumor, glioma of the brain stem, glioma, childhood cerebral astrocytoma, childhood visual pathway and hypothalamic glioma, gastric carcinoid, hairy cell leukemia, head and neck cancer, heart cancer, hepatocellular (liver) cancer, Hodgkin lymphoma, hypopharyngeal cancer, hypothalamic and visual pathway glioma, childhood intraocular melanoma, islet cell carcinoma (endocrine pancreas), kaposi sarcoma, kidney cancer (renal cell cancer), laryngeal cancer, leukemia, acute lymphoblastic (also called acute lymphocytic leukemia) leukemia, acute myeloid (also called acute myelogenous leukemia) leukemia, chronic lymphocytic (also called chronic lymphocytic leukemia) leukemia, chronic myelogenous (also called chronic myeloid leukemia) leukemia, hairy cell lip and oral cavity cancer, liposarcoma, liver cancer (primary), non-small cell lung cancer, small cell lung cancer, lymphomas, AIDS-related lymphoma, Burkitt lymphoma, cutaneous T-cell lymphoma, Hodgkin lymphoma, Non-Hodgkin (an old classification of all lymphomas except Hodgkin's) lymphoma, primary central nervous system lymphoma, Waldenstrom macroglobulinemia, malignant fibrous histiocytoma of bone/osteosarcoma, childhood medulloblastoma, melanoma, intraocular (eye) melanoma, merkel cell carcinoma, adult malignant mesothelioma, childhood mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, adult acute myeloid leukemia, childhood acute myeloid leukemia, multiple myeloma, chronic myeloproliferative disorders, nasal cavity and paranasal sinus cancer, nasopharyngeal carcinoma, neuroblastoma, oral cancer, oropharyngeal cancer, osteosarcoma/malignant, fibrous histiocytoma of bone, ovarian cancer, ovarian epithelial cancer (surface epithelial-stromal tumor), ovarian germ cell tumor, ovarian low malignant potential tumor, pancreatic cancer, islet cell paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, childhood pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, childhood Salivary gland cancer Sarcoma, Ewing family of tumors, Kaposi sarcoma, soft tissue sarcoma, uterine sezary syndrome sarcoma, skin cancer (nonmelanoma), skin cancer (melanoma), skin carcinoma, Merkel cell small cell lung cancer, small intestine cancer, soft tissue sarcoma, squamous cell carcinoma. squamous neck cancer with occult primary, metastatic stomach cancer, supratentorial primitive neuroectodermal tumor, childhood T-cell lymphoma, testicular cancer, throat cancer, thymoma, childhood thymoma, thymic carcinoma, thyroid cancer, urethral cancer, uterine cancer, endometrial uterine sarcoma, vaginal cancer, visual pathway and hypothalamic glioma, childhood vulvar cancer, and wilms tumor (kidney cancer).

X. Kits

Certain aspects of the present invention also concern kits containing compositions of the disclosure or compositions to implement methods of the invention. In some aspects, kits can be used to evaluate one or more biomarkers or HLA types. In certain aspects, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein.

Kits may comprise components, which may be individually packaged or placed in a container, such as a tube, bottle, vial, syringe, or other suitable container means.

Individual components may also be provided in a kit in concentrated amounts; in some aspects, a component is provided individually in the same concentration as it would be in a solution with other components. Concentrations of components may be provided as 1×, 2×, 5×, 10×, or 20× or more.

In certain aspects, negative and/or positive control nucleic acids, probes, and inhibitors are included in some kit aspects. In addition, a kit may include a sample that is a negative or positive control for methylation of one or more biomarkers.

It is contemplated that any method or composition described herein can be implemented with respect to any other method or composition described herein and that different aspects may be combined. The claims originally filed are contemplated to cover claims that are multiply dependent on any filed claim or combination of filed claims.

XI. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 4:
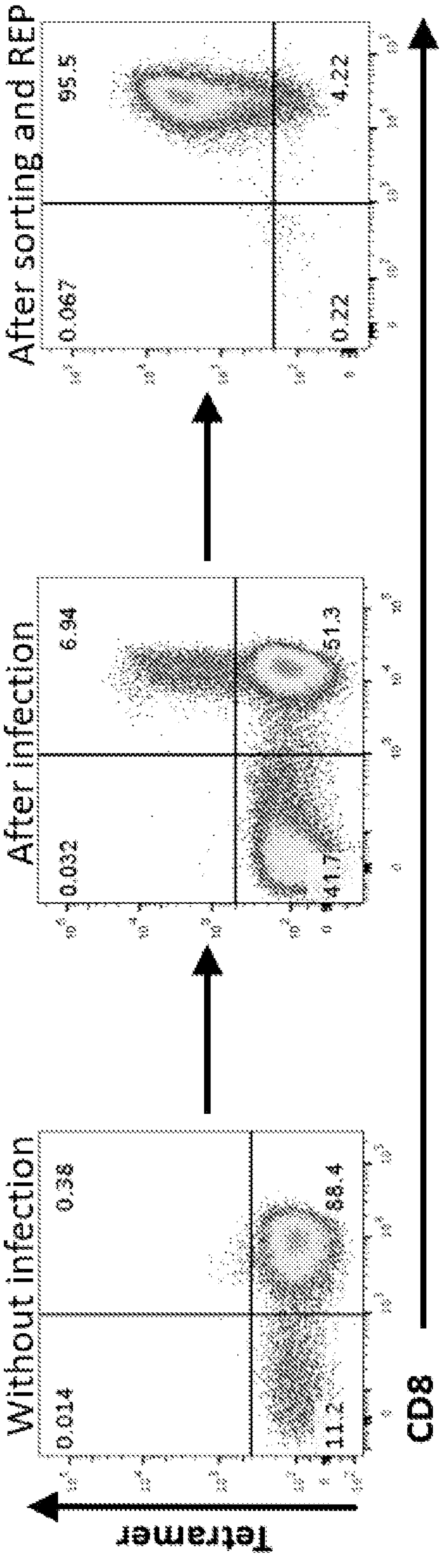
FIG. 4. COL6A3-642 specific TCR-T generation. The whole length TCR alpha chain and beta chain from COL6A3-642 C4 CTL cell line were assembled with P2A skip peptide and inserted into retrovirus vector pMSGV3. The recombinant retrovirus vector were used to infect the PBMC derived from HLA-A0201+ healthy donor. After infection, the CD8+/Tetramer+ population was appeared compared with the PBMC without infection. After tetramer guided sorting and expansion, the high purity of TCR-T was generated.
Figure 5:
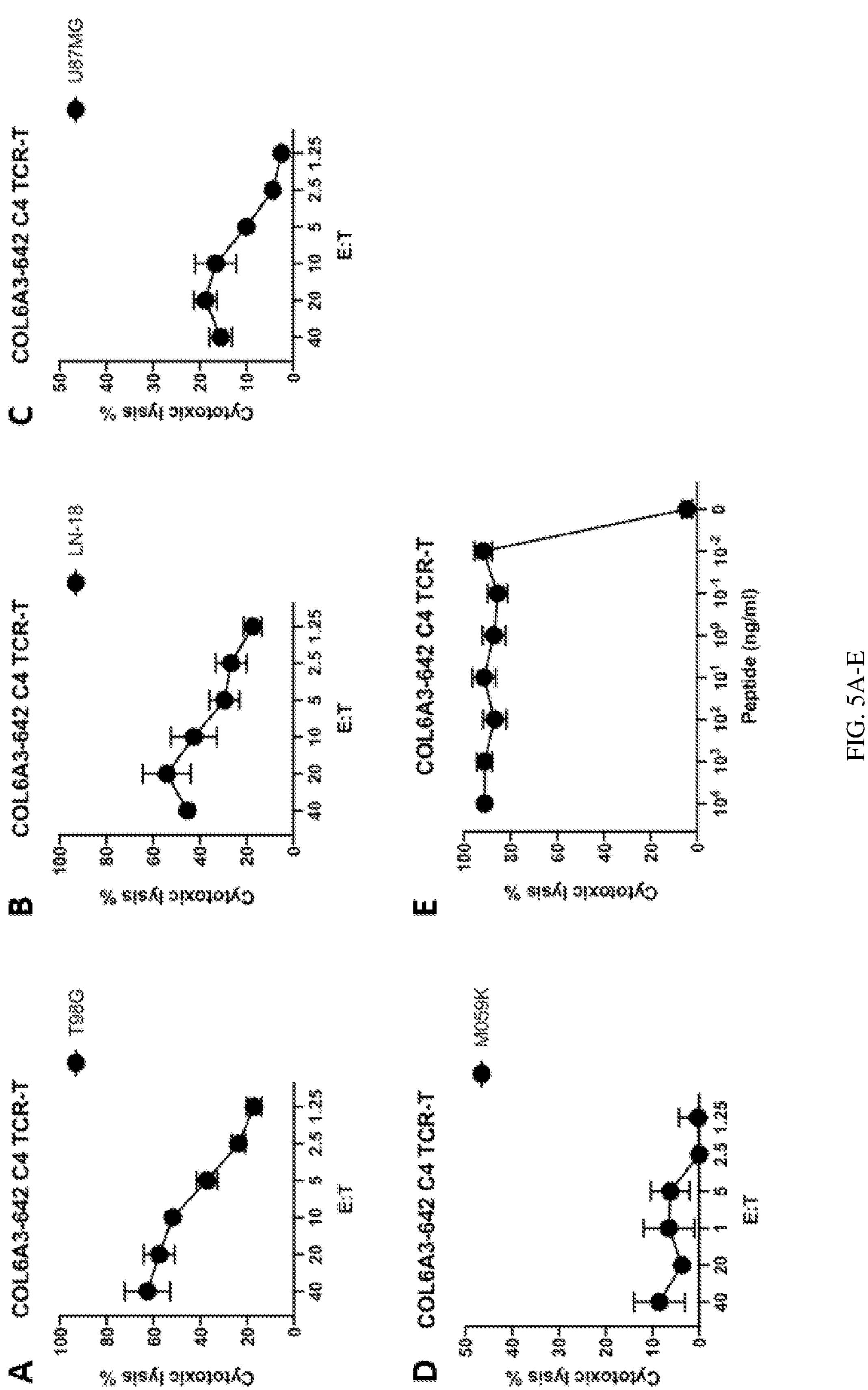
FIG. 5A-E. Functional validation of COL6A3-642 specific TCR-T cell lines. (A-D), different tumor targets were co-cultured with COL6A3-642 specific TCR-T cell line. The lysis ability of COL6A3-642 TCR-T cell lines were detected with Cr51 release assay (CRA). The effector to target (E:T) ratio is from 40:1 to 1.25:1. The COL6A3-642 TCR-T cell lines could effectively lysis the positive targets T98G, LN-18 and U87MG, but not for the negative target M095K. (E), T2 cells pulsed with various concentrations of COL6A3-642 peptide were used as target and co-cultured with COL6A3-642 TCR-T. The effector to target (E:T) ratio is 20:1. The COL6A3-642 TCR-T cell lines could effectively lysis the targets even at very low peptide concentration (10 pg/ml).
Figure 6:
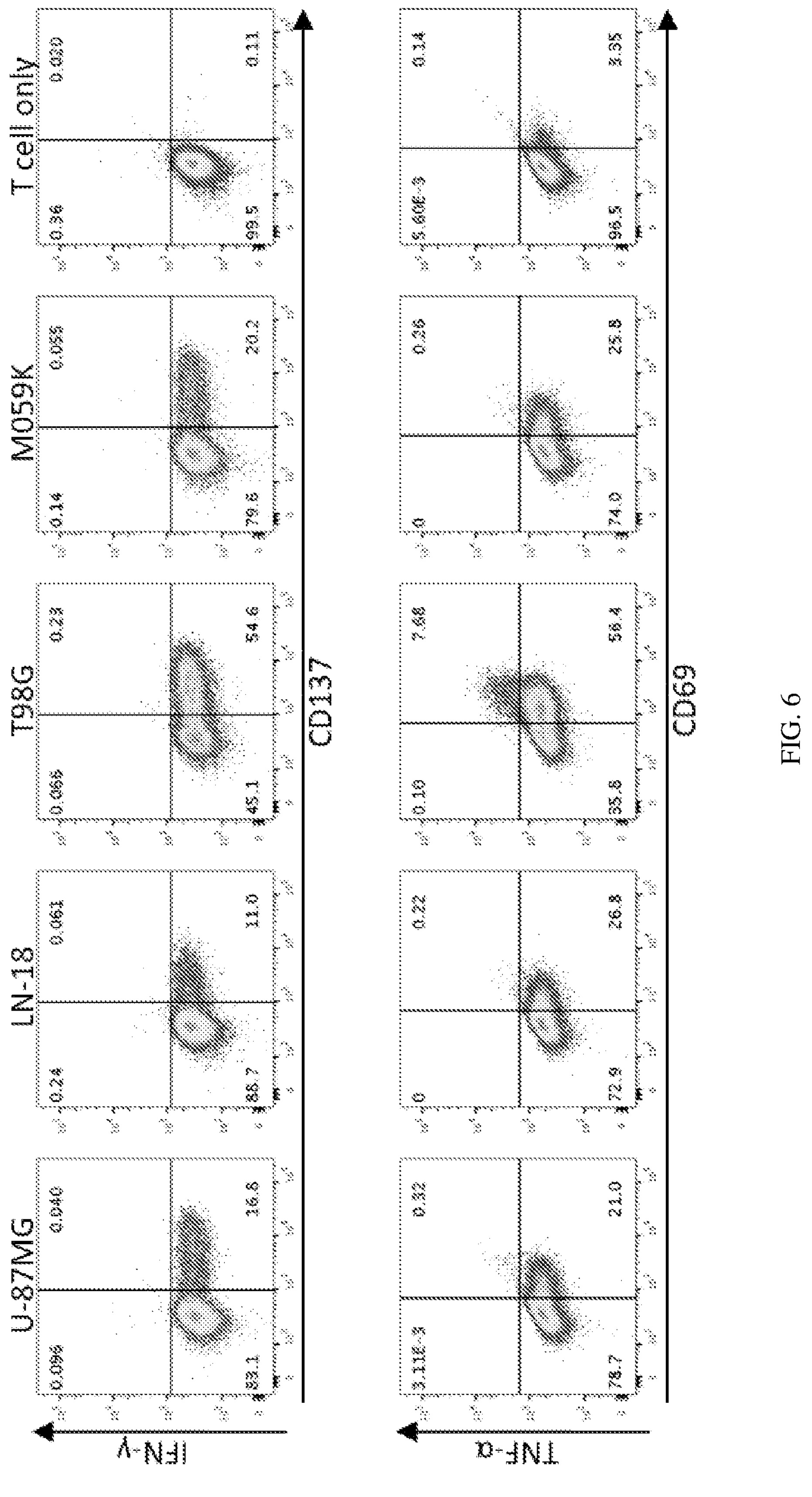
FIG. 6. Functional detection of COL6A3-642 TCR-T with intracellular cytokine staining (ICS) assay. The COL6A3-642 TCR-T cell line was co-cultured with tumor targets U87MG, LN-18, T98G, M059K with E:T=10:1 ratio. After overnight co-culturing, the TCR pathway down-stream activated marker, CD137, CD69, IFN-γ and TNF-α were detected with ICS assay. the level of CD137, CD69, IFN-γ and TNF-α of COL6A3-642 TCR-T were significantly enhanced when the cell lines were co-cultured with positive targets, especially T98G, compared with negative target.

Example 1: Generating of TCR Gene Modified T Cells with this TCR Sequence for Adoptive T Cell Therapy for Treatment of HLA-A2 Positive Cancer Patients A HLA-A2 restricted epitope (amino acid sequence is FLLDGSANV (SEQ ID NO:15)) from human tumor antigen COL6A3 has been found before. Here, we describe tools that can be used to target this epitope, such as engineered TCRs and cells harboring those TCRs. Using this peptide and corresponding tetramer, the inventors successfully generated an antigen-specific CTL cell line in vitro (FIG. 1), which can kill the tumor cells naturally presenting this peptide (FIG. 2-3). Based on this finding, the inventors cloned out the TCR sequence (including TCR alpha chain and beta chain) from the CTL cell line, and then constructed a retrovirus vector containing whole length of TCR alpha chain and beta chain with the linker, which can express both chains equally. Using this retrovirus vector, the inventors successfully introduced this TCR into allogenic peripheral blood mononuclear cells (PBMC) and generated antigen-specific TCR-T cell line (FIG. 4). This TCR-T cell line recognized its cognate epitope and killed tumor cells expressing COL6A3 antigen but not the negative control targets (FIG. 5-6). Base on the current work, the inventors plan to evaluate the safety and efficacy of this TCR-T therapy for the treatment of HLA-A*0201 positive patients with advanced or recurrent cancer in a nonrandomized dose-seeking Phase I/II study. On the basis of results obtained before, the inventors will generate and expand the TCR-T using patients' own PBMC. After functional detection (phenotype, killing ability, etc.), the TCR-T cells will be infused to patients with dose stepwise increased strategy to evaluate safety. If no serious dose limited toxicity (DTL) appears, anti-tumor efficacy will be determined further by staging evaluations and noted as a complete response (CR) partial response (PR) or progressive disease (PD) (RECIST criteria). At this period, the duration of persistence of transferred TCR-T will be determined. Progression-free survival will be also determined although it is not a primary endpoint in Phase I study. If no serious side effects appear and primary clinical response are observed, we will plan to apply a phase II study to further evaluate the efficacy of this TCR-T cells with a larger cohort HLA-A2 advanced cancer patients.

TABLE 1

Tumor targets used for functional validation of COL6A3-642 specific CTL cell lines

| | U87 | T98G | LN-18 | M059K |
|---|---|---|---|---|
| Cancer | GBM | GBM | GBM | GBM |
| HLA-A | A0201 | A0201 | A0201 | A0201 |
| COL6A3 RNA level (TPM) | 442.883 | 852.098 | 429.46 | 0.448 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An engineered T-cell Receptor (TCR) comprising a TCR-a polypeptide and a TCR-b polypeptide, wherein the TCR-a polypeptide comprises a CDR1 comprising the amino acid sequence of SEQ ID NO:6, a CDR2 comprising the amino acid sequence of SEQ ID NO: 7, and a CDR3 comprising an amino acid sequence of SEQ ID NO:8, and the TCR-b polypeptide comprises a CDR1 comprising the amino acid sequence of SEQ ID NO: 12, a CDR2 comprising the amino acid sequence of SEQ ID NO: 13, and a CDR3 comprising an amino acid sequence of SEQ ID NO: 14.

2. A fusion protein comprising the TCR of claim 1 and a CD3 binding region.

3. One or more nucleic acids encoding the TCR of claim 1.

4. A nucleic acid vector comprising the one or more nucleic acids of claim 3.

5. An isolated cell comprising the one or more nucleic acids of claim 3.

6. A composition comprising the one or more nucleic acids of claim 3.

7. A method for treating cancer in a subject comprising administering the isolated cell of claim 5 to a subject in need thereof.

8. The TCR of claim 1, wherein the TCR-a polypeptide comprises an amino acid sequence with at least 90% sequence identity to SEQ ID NO:4 and the TCR-b polypeptide comprises an amino acid sequence with at least 90% sequence identity to SEQ ID NO: 10.

9. The TCR of claim 8, wherein the TCR-a polypeptide comprises the amino acid sequence of SEQ ID NO:4 and the TCR-b polypeptide comprises the amino acid sequence of SEQ ID NO: 10.

10. The TCR of claim 1, wherein the TCR-a polypeptide is amino-proximal to the TCR-b polypeptide.

11. The TCR of claim 1, wherein the TCR-b polypeptide is amino-proximal to the TCR-a polypeptide.

12. The isolated cell of claim 5, wherein the isolated cell comprises a hematopoietic stem or progenitor cell, a T cell, or an induced pluripotent stem cell (iPSC).

13. The isolated cell of claim 12, wherein the isolated cell comprises an invariant NK T (INKT) cell, a gamma-delta T cell, or a regulatory T cell.

14. The cell of claim 5, wherein the isolated cell is isolated from a cancer patient.

15. The one or more nucleic acids of claim 3, encoding the TCR-a polypeptide and the TCR-b polypeptide in a single nucleic acid.

16. The engineered TCR of claim 1, wherein the TCR is a single chain TCR.

* * * * *